United States Patent
Ruschel et al.

(10) Patent No.: US 10,537,567 B2
(45) Date of Patent: Jan. 21, 2020

(54) KINASE INHIBITORS FOR TREATMENT OF DISEASE

(71) Applicant: BioAxone BioSciences, Inc., Cambridge, MA (US)

(72) Inventors: Joerg Ruschel, Cambridge, MA (US); Matthew D. Abbinanti, Westford, MA (US); Kenneth M. Rosen, Milton, MA (US); Lisa McKerracher, Boston, MA (US)

(73) Assignee: BioAxone BioSciences, Inc., Boston, MA (US)

( * ) Notice: Subject to any disclaimer, the term of this patent is extended or adjusted under 35 U.S.C. 154(b) by 0 days.

(21) Appl. No.: 16/032,442

(22) Filed: Jul. 11, 2018

(65) Prior Publication Data

US 2019/0015404 A1 Jan. 17, 2019

Related U.S. Application Data

(60) Provisional application No. 62/531,322, filed on Jul. 11, 2017.

(51) Int. Cl.
| | | |
|---|---|---|
| *A61K 31/4725* | (2006.01) | |
| *A61K 9/00* | (2006.01) | |
| *A61K 31/5575* | (2006.01) | |
| *A61P 27/06* | (2006.01) | |

(52) U.S. Cl.
CPC ........ *A61K 31/4725* (2013.01); *A61K 9/0019* (2013.01); *A61K 9/0053* (2013.01); *A61K 31/5575* (2013.01); *A61P 27/06* (2018.01); *A61K 9/0048* (2013.01); *A61K 2300/00* (2013.01)

(58) Field of Classification Search
CPC ............ A61K 31/4725; A61K 31/5575; A61K 9/0019; A61K 9/0053; A61K 9/0048; A61P 27/06
See application file for complete search history.

(56) References Cited

U.S. PATENT DOCUMENTS

| | | |
|---|---|---|
| 3,539,573 A | 11/1970 | Schmutz et al. |
| 4,584,303 A | 4/1986 | Huang et al. |
| 4,678,783 A | 7/1987 | Hidaka et al. |
| 4,798,897 A | 1/1989 | Hidaka et al. |
| 4,849,521 A | 7/1989 | Kudzma et al. |
| 4,857,301 A | 8/1989 | Czarniecki et al. |
| 4,866,077 A | 9/1989 | Bogeso et al. |
| 4,933,353 A | 6/1990 | Jensen et al. |
| 4,997,834 A | 3/1991 | Muro et al. |
| 5,478,838 A | 12/1995 | Arita et al. |
| 5,496,846 A | 3/1996 | Wilson et al. |
| 5,741,792 A | 4/1998 | Kimball et al. |
| 5,906,819 A | 5/1999 | Kaibuchi et al. |
| 6,020,352 A | 2/2000 | Kapin et al. |
| 6,140,333 A | 10/2000 | Tsuchiya et al. |
| 6,169,097 B1 | 1/2001 | Janssens et al. |
| 6,218,410 B1 | 4/2001 | Uehata et al. |
| 6,297,228 B1 | 10/2001 | Clark |
| 6,506,901 B2 | 1/2003 | Steffan et al. |
| 6,545,022 B1 | 4/2003 | Bryans et al. |
| 6,906,061 B2 | 6/2005 | Uehata et al. |
| 7,169,783 B2 | 1/2007 | McKerracher et al. |
| 7,199,147 B2 | 4/2007 | Imazaki et al. |
| 7,572,913 B2 | 8/2009 | McKerracher et al. |
| 8,957,003 B2 | 2/2015 | Wu et al. |
| 9,687,483 B2 | 6/2017 | McKerracher et al. |
| 10,106,525 B2 | 10/2018 | Rosen et al. |
| 10,149,856 B2 | 12/2018 | Rosen et al. |
| 2003/0120511 A1 | 6/2003 | Legnini |
| 2011/0112035 A1 | 5/2011 | Jorgensen et al. |
| 2014/0256941 A1 | 9/2014 | Liu et al. |
| 2015/0297643 A1 | 10/2015 | McKerracher |
| 2016/0016914 A1 | 1/2016 | Ladziata et al. |
| 2016/0213664 A1 | 7/2016 | McKerracher et al. |
| 2017/0313680 A1 | 11/2017 | Rosen et al. |

FOREIGN PATENT DOCUMENTS

| | | |
|---|---|---|
| CA | 2304981 A1 | 5/1999 |
| CA | 2342251 A1 | 3/2000 |
| CA | 2443108 A1 | 10/2002 |
| CA | 2325842 C | 8/2007 |
| WO | WO-03/042174 A1 | 5/2003 |
| WO | WO-2015/165341 A1 | 11/2015 |
| WO | WO-2018/022927 A1 | 2/2018 |
| WO | WO-2018/118109 A1 | 6/2018 |

OTHER PUBLICATIONS

Demiryurek, Current Eye Research, 35(12), 1128-1134, 2010. (Year: 2010).*
Alexopoulos et al., "Design and synthesis of novel biologically active thrombin receptor non-peptide mimetics based on the pharmacophoric cluster Phe/Arg/NH2 of the Ser42-Phe-Leu-Leu-Arg46 motif sequence: platelet aggregation and relaxant activities," J. Med. Chem. 47(13):3338-52 (2004).
Berge et al., "Pharmaceutical salts," J Pharm Sci. 66(1):1-19 (1977).
Borikova et al., "Rho Kinase Inhibition Rescues the Endothelial Cell Cerebral Cavernous Malformation Phenotype," J Biol Chem. 285(16):11760-4 (2010).
del Peso et al., "Rho proteins induce metastatic properties in vivo," Oncogene. 15(25):3047-57 (1997).
Eldawoody et al., "Simplified experimental cerebral aneurysm model in rats: comprehensive evaluation of induced aneurysms and arterial changes in the circle of Willis," Brain Res. 1300:159-68 (2009).
FDA, Guidance for Industry "Estimating the Maximum Safe Starting Dose in Initial Clinical Trials for Therapeutics in Adult Healthy Volunteers," (2005) (30 pages).
Fukumoto et al., "Acute vasodilator effects of a Rho-kinase inhibitor, fasudil, in patients with severe pulmonary hypertension," Heart. 91:391-2 (2005).

(Continued)

*Primary Examiner* — D Margaret M Seaman
(74) *Attorney, Agent, or Firm* — Clark & Elbing LLP

(57) ABSTRACT

Disclosed are therapeutic compositions including BA-1076 and/or BA-2057, methods of their use in the treatment of ophthalmological disorders. The therapeutic compositions may further include an IOP-lowering prostaglandin. The methods may further include administration of an IOP-lowering prostaglandin.

19 Claims, 18 Drawing Sheets

(56) References Cited

OTHER PUBLICATIONS

Hahmann et al., "Rho-kinase inhibitors as therapeutics: from pan inhibition to isoform selectivity," Cell. Mol. Life Sci. 67:171-177 (2010).
Haskins, "The application of stable isotopes in biomedical research," Biomed Mass Spectrom. 9(7):269-77 (1982).
International Search Report for International Patent Application No. PCT/US2018/041597, dated Oct. 4, 2018 (5 pages).
International Search Report for International Patent Application No. PCT/US2017/031836, dated Oct. 2, 2017 (5 pages).
Ishizaki et al., "p160ROCK, a Rho-associated coiled-coil forming protein kinase, works downstream of Rho and induces focal adhesions," FEBS Lett. 404(2-3):118-24 (1997).
Ishizaki et al., "Pharmacological Properties of Y-27632, a Specific Inhibitor of Rho-Associated Kinases," Mol. Pharmacol. 57(5):976-83 (2000).
Ishizaki et al., "The small GTP-binding protein Rho binds to and activates a 160 kDa Ser/Thr protein kinase homologous to myotonic dystrophy kinase," EMBO. 15(8):1885-1893 (1996).
Jacobs et al., "The Structure of Dimeric ROCKI Reveals the Mechanism for Ligand Selectivity," J. Biolog. Chem. 281(1):260-8 (2006).
Jick et al., "Statins and the risk of dementia," Lancet. 356(9242):1627-31 (2000).
Kast et al., "Cardiovascular effects of a novel potent and highly selective azaindole-based inhibitor of Rho-kinase," Brit. J. Pharmacol. 152(7):1070-80 (2007).
Kato et al., "Statin blocks Rho/Rho-kinase signalling and disrupts the actin cytoskeleton: relationship to enhancement of LPS-mediated nitric oxide synthesis in vascular smooth muscle cells," Biochim Biophys Acta. 1689(3):267-72 (2004).
Lee et al., "Neurodegenerative Tauopathies," Annu Rev Neurosci. 24:1121-59 (2001) (41 pages).
Lee et al., "Selective ROCK2 inhibition in focal cerebral ischemia." Ann. Clin. Transl. Neurol. 1(1):2-14 (2014).
Leemhuis et al., "The protein kinase A inhibitor H89 acts on cell morphology by inhibiting Rho kinase," J. Pharmacol. Exp. Ther. 300(3):1000-7 (2002).
McGeer et al., "Anti-inflammatory drugs and Alzheimer disease," Lancet. 335(8696): 1037 (1990).
McKerracher et al., "Identification of myelin-associated glycoprotein as a major myelin-derived inhibitor of neurite growth," Neuron. 13(4):805-11 (1994).
Mertsch et al., "Opposing Signaling of ROCK1 and ROCK2 Determines the Switching of Substrate Specificity and the Mode of Migration of Glioblastoma Cells," Mol. Neurobiol. 49(2):900-15 (2014).
Nakagawa et al., "ROCK-I and ROCK-II, two isoforms of Rho-associated coiled-coil forming protein serine/threonine kinase in mice." FEBS. Lett. 392(2):189-93 (1996).
Newell-Litwa et al., "ROCK1 and 2 differentially regulate actomyosin organization to drive cell and synaptic polarity," J Cell Biol. 210(2):225-42 (2015).
Pelosi et al., "ROCK2 and Its Alternatively Spliced Isoform ROCK2m Positively Control the Maturation of the Myogenic Program," Mol Cell Biol. 27(17):6163-76 (2007).
Rikitake et al., "Inhibition of Rho Kinase (ROCK) Leads to Increased Cerebral Blood Flow and Stroke Protection," Stroke. 36(10):2251-7 (2005).
Sayas et al., "Glycogen synthase kinase-3 is activated in neuronal cells by Galpha12 and Galpha13 by Rho-independent and Rho-dependent mechanisms," J. Neurosci. 22(16):6863-75 (2002).
Shi et al., "Distinct roles for ROCK1 and ROCK2 in the regulation of cell detachment." Cell Death and Disease 4:e483 (2013).
Shi et al., "Rho Kinases in Cardiovascular Physiology and Pathophysiology: The Effect of Fasudil," available in PMC Oct. 1, 2014, published in final edited form as J Cardiovasc Pharmacol. 62(4):341-54 (2013) (32 pages).
Weggen et al., "A subset of NSAIDs lower amyloidogenic Abeta42 independently of cyclooxygenase activity," Nature. 414(6860):212-6 (2001).
Wibberley et al., "Expression and functional role of Rho-kinase in rat urinary bladder smooth muscle," Br. J. Pharmacol. 138(5):757-66 (2003).
Yi et al., "Photoactivation of hypericin decreases the viability of RINm5F insulinoma cells through reduction in JNK/ERK phosphorylation and elevation of caspase-9/caspase-3 cleavage and Bax-to-Bcl-2 ratio." Biosci Rep. 35(3):e00195 (2015) (13 pages).
Zhao et al., "Efficacy and safety of fasudil in patients with subarachnoid hemorrhage: final results of a randomized trial of fasudil versus nimodipine," Neurol Med Chir. 51(10):679-83 (2011).
Zhou et al., "Nonsteroidal anti-inflammatory drugs can lower amyloidogenic Abeta42 by inhibiting Rho," Science. 302(5648):1215-7 (2003) (4 pages).

\* cited by examiner

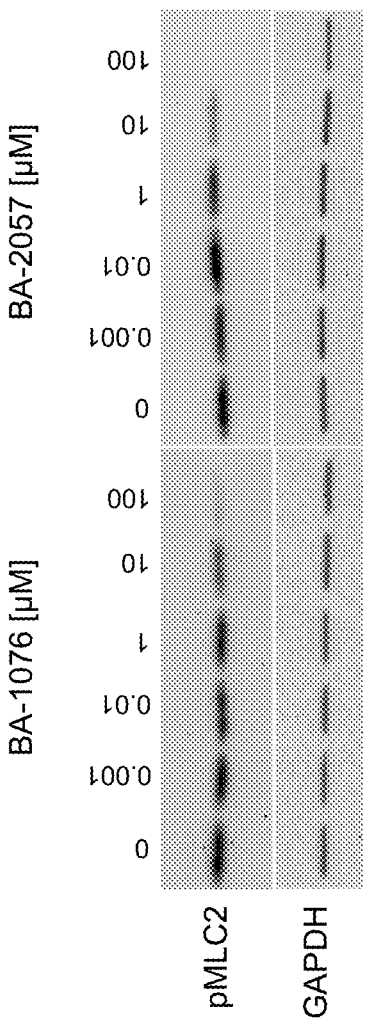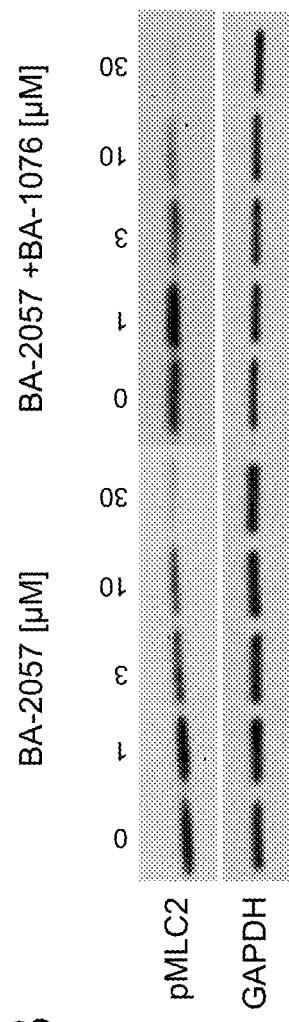
FIG. 5A
FIG. 5B

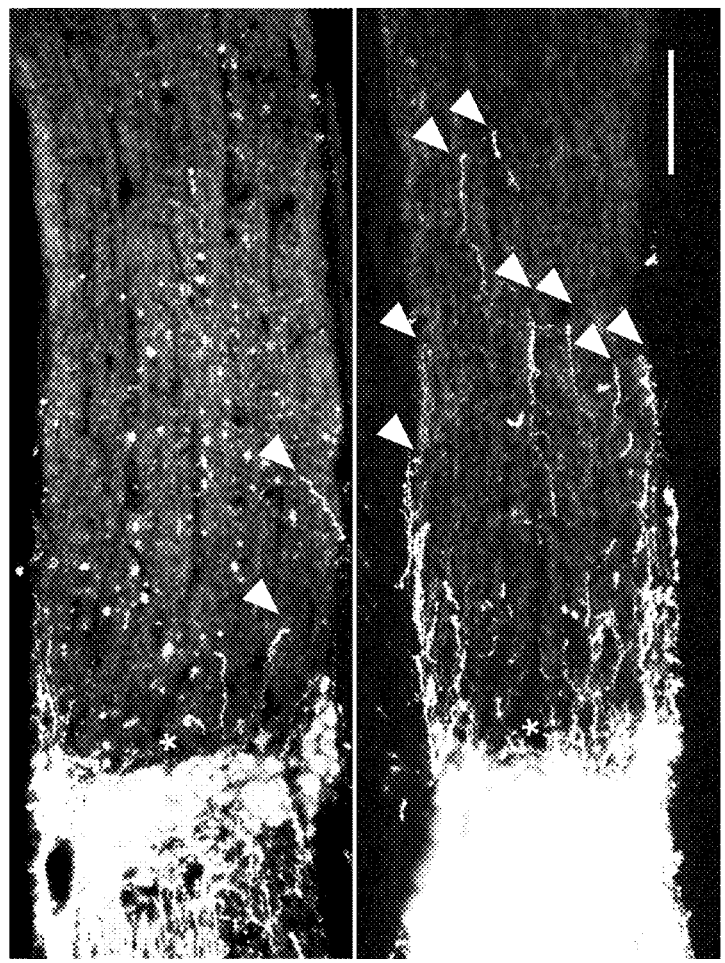

KINASE INHIBITORS FOR TREATMENT OF DISEASE

FIELD OF THE INVENTION

This invention relates to novel kinase inhibitors for treatment of diseases of the nervous system, ophthalmological indications and gastrointestinal disorders.

BACKGROUND

Rho kinase (ROCK) is a kinase found in all eukaryotic cells. It regulates key processes that include cell motility, cell differentiation, cell survival, cell-cell junctions and expression of extracellular matrix proteins. There are two isoforms of ROCK, ROCK1 and ROCK2. ROCK2 is more highly expressed in the CNS. It is also the form most highly expressed in tissues that have dysregulated ROCK in disease. Therefore ROCK-2 selective inhibitors may be used to treat a variety of diseases accompanied by abnormal or pathological activation of ROCK signaling for instance inflammatory stimuli, the microbiome or other factors that increase the activity of ROCK2 leading to progression of disease.

The Abl tyrosine kinase was identified as a critical driver of leukemia from studies of the Abelson murine lymphosarcoma virus that induced cellular transformation and lymphomas. Subsequent studies demonstrated that chromosomal translocation of ABL1 to the breakpoint cluster region (BCR) gene sequences results in production of the BCR-ABL1 fusion protein and elevated tyrosine kinase activity in patients with Philadelphia (Ph) chromosome-positive human leukemia. Subsequently studies of Abl show that, like ROCK, it regulates many cellular processes leading to disease. Abl is not typically active in neurons, but is activated in many neurological diseases. Abl regulates diverse cellular processes and can be activated by multiple stimuli leading to cytoskeletal reorganization and cell survival. There are two isoforms of Abl: Abl1 and Abl2. Abl1 is the form of interest for this application. It is sometimes called c-Abl or Abl in the literature, and we refer to it as Abl.

An off-target activity of a ROCK2 inhibitor on Abl kinase may be of benefit in treating ophthalmological diseases of retinal ganglion cells. ROCK2 and Abl are key kinases that regulate homeostatic balance of the cytoskeleton, and their perturbation and kinase hyper-activation causes neuronal dysfunction and cell death. The neuronal cytoskeleton of projection neurons such as retinal ganglion cells is particularly susceptible to disturbances in cytoskeletal regulation because of the long axonal process and requirement for axonal transport. If a retinal ganglion cells was the size of a Volkswagen Beetle, its axon would be 2 miles long.

Ophthalmology

Glaucoma is a disease that affects retinal ganglion cells (RGCs), and changes at the optic nerve head where the RGC axons exit the retina are one of the first visual hallmarks of disease (Quigley. 2016 Annu Rev Vis Sci. 2: p. 235-254). It has been estimated that glaucoma will affect more than 80 million individuals worldwide by 2020, with 6-8 million individuals becoming bilaterally blind. Glaucoma is the second leading cause of irreversible blindness, one of the most prevalent neurodegenerative diseases. Glaucoma starts with a loss of peripheral vision and painlessly progresses slowly, eventually leading to vision loss, then blindness. Visual loss results from loss of RGCs, and that reduced aqueous humor drainage through the trabecular meshwork (TM) and Schlemm's canal is the root cause of ocular hypertension in glaucoma. In the initial stages, activities involving glare and dark adaption are affected which impacts driving and mobility; motor accidents and falls are early consequences of glaucoma. The total annual economic impact of visual disorders to the healthcare system for Americans aged 40 years and older is estimated at $35 billion.

Many forms of glaucoma are associated with elevated intraocular pressure (IOP) and standard treatment is to reduce IOP with drugs. Because progression of glaucoma is slow and painless, noncompliance for daily use of IOP-reducing medications is high. Side-effects make non-compliance even more likely because there is no immediate impact when eye drops are not applied. Even with daily treatments, some patients show continuous progression of glaucoma despite reaching their lowest achievable IOP (Chang et al. 2012 Ophthal. 119(5): p. 978-986). Failure to keep IOP reduced results in irreversible damage, and patients do not lose vision until there is permanent neuronal loss. Lowering intraocular pressure slows the progression of disease, but lowering IOP does not address the underlying mechanism of RGC death and optic nerve degeneration. Therefore, glaucoma is controlled, but never cured by daily use of available eye drops that reduce IOP.

There are six classes of topical ocular hypotensive drugs used to lower IOP. Prostaglandin analogs are the biologically active metabolites of arachidonic acid and its analogs that are commonly used to reduce IOP. They may reduce IOP by 27%-33%, typically require once daily dosing, and are generally associated with good compliance. Rho kinase (ROCK) inhibitors have potential to slow blockage of the TM by reducing fibrosis, thereby slowing RGC death. However, non-specific ROCK inhibitors in clinical development cause significant hyperemia, a side effect that leads to non-compliance, although long-term use would be needed to effectively slow disease progression. Non-specific ROCK inhibitors have been shown to be neuroprotective, but only by intravitreal injection (Kitaoka et al. 2014 Brain Res. 1018(1): p. 111-118), which is not a feasible delivery for repetitive treatment in humans. Thus, drugs that reduce IOP and slow disease progression are urgently needed to prevent blindness in glaucoma.

In the eye, the TM is a mechanosensitive structure that regulates aqueous humor outflow. Aqueous humor is produced by the ciliary body epithelium lining, and it drains out of the eye through the TM into Schlemm's canal and into the episcleral venous system. Glaucoma is believed to be associated with changes in the TM that increase deposition of extracellular matrix (ECM) adjacent to Schlemm's canal (Tektas et al. 2009 Exp Eye Res. 88(4): p. 769-775), a process regulated by ROCK (Pattabiraman, P. P. et al., 2016, Eur. J. of Pharm., 787: P. 32-42). Hyperactivation of ROCK may increase deposition ECM in human TM cells, slowing drainage (Pattabiraman et al. 2014 J Cell Physio. 229(7): p. 927-942). Thus, ROCK inhibitors that suppress fibrogenic activity of TM cells would loosen the TM to increase aqueous humor outflow and reduce IOP.

There are two forms of ROCK that may be implicated in glaucoma. The TM has both ROCK1 and ROCK2 and RGCs have more ROCK2. ROCK2 is more important for RGC regeneration (U.S. Pat. No. 7,572,913., 2009). Y-27632 and Fasudil, targeting both ROCKs are the most widely used reference ROCK inhibitors for research. There have been 7 different ROCK inhibitors tested in human clinical trials, most with equal affinity to ROCK1 and ROCK2 (Ren et al. 2016 Invest ophthal Vis Sci. 57(14):p. 6197-6209). Lack of therapeutic window has hampered the development of ROCK inhibitors, even when used topically to treat eye diseases (Defert et al. 2017 Expert Opin Ther Pat. 27:507-515).

ROCK inhibitors may reduce IOP by increasing aqueous humor outflow through the TM, by contrast to available IOP-reducing drugs that act on the unconventional pathway of uveoscleral drainage (Whitlock et al. 2009 J Ocul Pharmacol Ther. 25(3): p. 187-194). Rho/ROCK pathway is often activated in disease, and they also have potential to be neuroprotective and increase plasticity and regeneration of RGC injury. Netarsudil (previously AR-33324) is the only ROCK inhibitor approved in the USA. Ripasudil is approved in Japan, but not the USA. Both inhibitors cause hyperemia (red eyes) as a major side effect (Bacharach et al. 2015 Ophthalmology 122(2): p. 302-307., Tanihara H. et al. 2016 Acta ophthalmol. 94(1): p. e26-e34), and therefore patient compliance is expected to be problematic.

There is a need for ROCK inhibitors causing reduced or no hyperemia. There is a need for newdisease-modifying treatments for glaucoma.

Retinitis pigmentosa (RP) is a degenerative retinal dystrophy caused by the progressive degeneration of the rod photoreceptor cells in the retina. This form of retinal dystrophy manifests initial symptoms independent of age. The progressive rod degeneration is followed by abnormalities in the adjacent retinal pigment epithelium (RPE) and the deterioration of cone photoreceptor cells. As peripheral vision becomes increasingly compromised, patients experience progressive "tunnel vision" and eventual blindness. Affected individuals may additionally experience defective light-dark adaptations, nyctalopia (night blindness), and the accumulation of bone spicules in the fundus. RP is relatively rare inherited disorder that results from mutations in any one of more than 50 genes required for making proteins that are needed in functioning photoreceptor cells.

Macular degeneration, also known as age-related macular degeneration (AMD or ARMD), is an eye disorder affecting over 235 million people world-wide. Macular degeneration results in blurred or no vision in the center of the visual field, but does not result in complete blindness. Visual hallucinations may also occur but these do not represent a mental illness. Macular degeneration is the result of damage to the macula of the retina. It may be age-related, but genetic factors and smoking also play a role. The severity is divided into early, intermediate, and late types, with the late type being further divided into "dry" and "wet" forms. The dry form makes up 90% of cases. Supplements in those who already have the disease may slow progression, but there is no cure or treatment that returns vision already lost. In the wet form, anti-VEGF medication injected into the eye or less commonly laser coagulation or photodynamic therapy may slow worsening. Targeting VEGF may reduce pathological growth of blood vessels in the retina that contribute to pathology of disease.

There is a need for new therapies for retinitis pigmentosa, macular degeneration, and retinal angiogenesis.

Diseases affecting the cornea are a major cause of blindness worldwide, second only to cataract in overall importance. The epidemiology of corneal blindness is complicated and encompasses a wide variety of infectious and inflammatory eye diseases that cause corneal opacity and scarring, which ultimately leads to functional blindness. There have been a number of studies that indicate potential usefulness of ROCK inhibitors for treatment of corneal diseases that include Fuchs' corneal dystrophy, corneal scarring, and prevention of scaring complication in glaucoma surgery.

Fuchs' corneal dystrophy is a progressive, hereditary disease of the cornea which is late onset and slowly progressing. Patients often present in the fifth to sixth decade of life with blurry morning vision that increases in duration as the disease progresses. Symptoms at presentation include painless decrease in visual acuity, photophobia, glare and halos around lights. It is a condition of the posterior cornea and characteristic features include the formation of focal excrescences of Descemet membrane termed 'guttae', and loss of endothelial cell density. As disease advances, corneal edema results in the development of painful subepithelial and epithelial bullae, and may progress to loss of corneal sensation, visual acuity and, ultimately, the development of corneal opacification and pannus formation. The ROCK inhibitor Y27432 has been used to treat patients with Fuchs membrane dystrophy. Upon treatment corneal clarity improved and vision improved for the 24 months the patient was followed (Norika et al 2013. Cornea 32:1167-1170). ROCK inhibitors inhibit keratocyte-to-myofibroblast transition, and topical application after a superficial lamellar keratectomy elicits an altered wound healing response, with evidence of an embryonic-type deposition of collagen fibrils thus avoiding scar tissue formation in preference to an ordered regeneration of the wounded tissue (Yamamoto 2012. Mol Vis. 18:1727-1739).

In the surgical treatment for glaucoma, the most common complication of glaucoma surgery is scar formation induced by activation of a wound healing response that causes fibrosis at the surgical site. Rho kinase inhibitors reduce activation of human conjunctival fibroblasts and that treatment with Rho kinase inhibitor via eyedrops significantly suppresses scar formation (Futakuchi et al. 2016. Experimental eye research. 149:107-115). Similarily, BA-1076 will be of therapeutic use in preventing excessive scarring after glaucoma filtration surgery.

There is a need for new therapies for the treatment of corneal blindness, Fuchs' corneal dystrophy, and corneal scarring, and for reducing post-operative scarring (e.g., post-glaucoma surgery corneal scarring).

Gastrointestinal Disorders

Tight junctions are crucial determinants of barrier function in polarized intestinal epithelia and are significantly regulated by activity of the Rho-ROCK pathway (Walsh et al., Gastroenterology, 2001; 121(3):566). Many conditions can impact negatively on barrier function in the intestinal epithelium ranging from inflammation to radiation exposure. It is also known that inhibition of the Rho-ROCK pathway can limit the activation of pro-fibrotic pathways, such as are activated in the setting of inflammatory bowel disorders, and positively impact on paracellular permeability through tight junctions (Du et al., Gastroent. Res. Pract.; 2016; 2016: 7374197). Importantly, evidence has also suggested that inhibition of the c-Abl signaling pathway may also show anti-fibrotic effects. Having an inhibitor targeting both ROCK and c-Abl may provide a novel therapeutic approach in this setting.

Ionizing radiation can be emitted from atoms of radioactive isotopes and can be released accidently (e.g., nuclear accident), by medical procedure (e.g., radiation treatment of cancer) or by bombs during war. Radiation is a high-energy particle or electromagnetic radiation that deposits energy when it interacts with atoms, resulting in ionization (electron excitation). As a result, an affected cell may either die or malfunction. The radiation can damage a cell directly by DNA damage, or indirectly through the creation of unstable, toxic hyperoxide molecules; which in turn can damage sensitive molecules and afflict subcellular structures. Radiation damage primarily affect proliferating cells, and the cell intestine has a very low threshold to radiation damage because of fast cell turnover. Bone marrow tissue is also sensitive. Symptoms of acute radiation poisoning are dependent on the absorbed dose, with symptoms appearing hours to days. There are treatments for the hematologic disorders that follow radiation poisoning (e.g., bone marrow transplants, and treatment with G-CSF (Neupogen). There are no effective treatments for the gastrointestinal (GI) disorders in ARS.

The polarized cells epithelial cells of the GI tract that form a protective barrier against commensal and pathogenic microorganisms play an important barrier function, in addition to their role in regulating absorption of nutrients, water, and ion homeostatic. GI-acute radiation syndrome (ARS) the destruction of the intestinal epithelial lining causes breakdown of the mucosal barrier, resulting in diarrhea, dehydration and electrolyte imbalance. Although all cellular compartments may contribute to and modulate organ dysfunction, the key event in the pathophysiology of intestinal radiation toxicity is enterocyte depletion, with possible vascular damage contributing at higher radiation doses. IN GI-ARS there is loss of intestinal clonic cells, leading to loss of epithelia crypts. The severity of mucosal breakdown is dose dependent, and occurs at radiation levels higher than those that destroy bone marrow. In the highly polarized epithelial cells of the GI tract, maintaining the correct balance of active and inactive ROCK is critical to function of the tissue. Over activation of Rho cause loss of barrier function because it is a key regulator of adherens and tight junctions. The ROCK pathway has been identified as a target of for modulation of intestinal radiation-induced toxicity (Haydont et al, British Journal of Radiology, 80 (2007), S32-S40).

SUMMARY

In general, the invention provides compounds, compositions, and methods of medical use.

In one aspect, the invention provides therapeutic compositions including a therapeutically effective amount of a compound of formula:

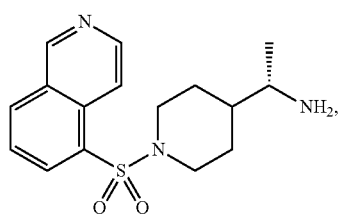

BA-1076 or a pharmaceutically acceptable salt thereof, where BA-1076 is stereochemically enriched (e.g., BA-1076 or a pharmaceutically acceptable salt thereof is present in at least 10% ee, at least 50% ee, at least 75% ee, at least 80% ee, at least 90% ee, at least 95% ee, or at least 98% ee). Preferably, BA-1076 or a pharmaceutically acceptable salt thereof is present in at least 90% ee. More preferably, BA-1076 or a pharmaceutically acceptable salt thereof is present in at least 95% ee.

In another aspect, the invention provides therapeutic compositions including a therapeutically effective amount of a compound of formula:

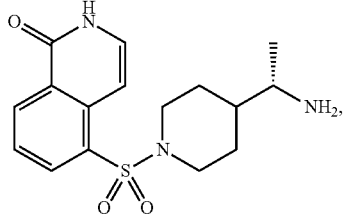

BA-2057 or a pharmaceutically acceptable salt thereof, where BA-2057 is stereochemically enriched (e.g., BA-2057 or a pharmaceutically acceptable salt thereof is present in at least 10% ee, at least 50% ee, at least 75% ee, at least 80% ee, at least 90% ee, at least 95% ee, or at least 98% ee). Preferably, BA-2057 or a pharmaceutically acceptable salt thereof is present in at least 90% ee. More preferably, BA-2057 or a pharmaceutically acceptable salt thereof is present in at least 95% ee.

In some embodiments, the therapeutic composition comprises BA-1076, or a pharmaceutically acceptable salt thereof, and BA-2057, or a pharmaceutically acceptable salt thereof. In certain embodiments, the therapeutic composition is formulated for ocular topical administration, intravitreal administration, intraocular administration, retinal administration, oral administration, or intravenous administration. In further embodiments, the therapeutic composition is in a dosage form of eye drops. In yet further embodiments, the therapeutic composition includes the compound at a concentration of 0.001% to 5% (w/v). In still further embodiments, the therapeutic composition is formulated for oral administration. In other embodiments, the therapeutic composition comprises the compound at a dose of 0.01 mg/kg to 10 mg/kg. In yet other embodiments, the therapeutic composition is formulated for intravenous administration. In still other embodiments, the therapeutic composition comprises the compound at a dose of 0.001 mg/kg to 1 mg/kg. In some embodiments, the therapeutic composition further includes an IOP-lowering prostaglandin. In particular embodiments, the IOP-lowering prostaglandin is Travaprost (e.g., TRAVATAN®), Bimatoprost (e.g., LUMIGAN®), Latanoprost (e.g., XALATAN®), or Tafluprost (e.g., ZIOPTAN®). In certain embodiments, the prostaglandin analog is Latanoprost (e.g., XALATAN®).

Inhibitors of ROCK2 (and optionally Abl) described herein may be useful in treating neurological disorders including Alzheimer's Disease, Parkinson's Disease, ALS, stroke, and spinal cord injury and neurotrauma.

Certain inhibitors of ROCK, alone or in combination with IOP-lowering prostaglandins, may be useful for treatment of eye pathologies including glaucoma, retinitis pigmentosa, macular degeneration, retinal angiogenesis, corneal blindness, Fuchs' corneal dystrophy, and/or corneal scarring. These ROCK inhibitors may act by multiple mechanisms to slow disease progression.

In another aspect, the invention provides a method of treating Alzheimer's Disease, Parkinson's Disease, ALS, stroke, spinal cord injury, glaucoma, retinitis pigmentosa, macular degeneration, retinal angiogenesis, corneal blindness, Fuchs' corneal dystrophy, or corneal scarring in a subject in need thereof. Preferably, the method is for treating glaucoma, retinitis pigmentosa, macular degeneration, retinal angiogenesis, corneal blindness, Fuchs' corneal dystrophy, or corneal scarring. In a related aspect, the invention provides a method of reducing post-operative corneal scarring (e.g., post-glaucoma surgery corneal scarring) in a subject in need thereof.

The methods include, e.g., administering to the subject a therapeutically effective amount of a therapeutic composition of the invention (e.g., a therapeutic composition including BA-1076, or a pharmaceutically acceptable salt thereof, or BA-2057, or a pharmaceutically acceptable salt thereof). In some embodiments, the therapeutic composition is administered topically, intravitreally, intraocularly, retinally to the eye, orally, or intravenously. In certain embodiments (e.g., in the treatments of glaucoma, retinitis pigmentosa, macular degeneration, retinal angiogenesis, corneal blindness, Fuchs' corneal dystrophy, or corneal scarring), the therapeutic composition is administered topically to the eye. In particular embodiments, the therapeutic composition is administered orally. In further embodiments, the therapeutic composition is administered intravenously. In yet further embodiments, the method is for treating glaucoma in the subject. In still further embodiments, the method is for treating retinitis pigmentosa in the subject. In other embodiments, the method is for treating macular degeneration in the subject. In yet other embodiments, the method is for treating retinal angiogenesis in the subject. In still other embodiments, the method is for treating corneal blindness. In some embodiments, the method is for treating Fuchs' corneal dystrophy. In certain embodiments, the method is for treating corneal scarring.

In some embodiments (e.g., in the treatment of glaucoma), the method further includes administering an IOP-lowering prostaglandin (e.g., Travaprost (e.g., TRAVATAN®), Bimatoprost (e.g., LUMIGAN®, Latanoprost (e.g., XALATAN®), or Tafluprost (e.g., ZIOPTAN®)). In particular embodiments, the prostaglandin analog is Latanoprost (e.g., XALATAN®).

In some embodiments, BA-1076 or a pharmaceutically acceptable salt thereof is formulated as an oral tablet, e.g., for daily dosing. In certain embodiments, BA-2057 or a pharmaceutically acceptable salt thereof is CNS and/or retinal penetrant.

DEFINITIONS

The term "BA-1049," as used herein, refers to a compound of formula:

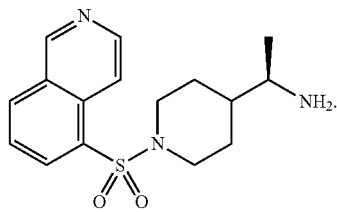 [SMILES: C[C@@H](N)C1CCN(S(=O)(=O)c2cccc3cnccc23)CC1]

In some embodiments, BA-1049 may be formulated and/or used as a pharmaceutically acceptable salt. In therapeutic compositions containing BA-1049, BA-1049 or a pharmaceutically acceptable salt thereof is stereochemically enriched (e.g., BA-1049 or a pharmaceutically acceptable salt thereof is present in at least 10% ee, at least 50% ee, at least 75% ee, at least 80% ee, at least 90% ee, at least 95% ee, or at least 98% ee). Preferably, BA-1049 or a pharmaceutically acceptable salt thereof is present in at least 90% ee. More preferably, BA-1049 or a pharmaceutically acceptable salt thereof is present in at least 95% ee.

The term "BA-1076," as used herein, refers to a compound of formula:

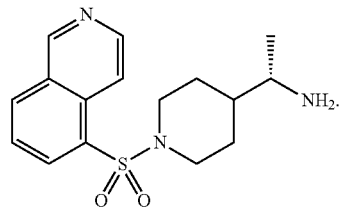 [SMILES: C[C@H](N)C1CCN(S(=O)(=O)c2cccc3cnccc23)CC1]

In some embodiments, BA-1076 may be formulated and/or used as a pharmaceutically acceptable salt. In some embodiments, BA-1076 may be formulated and/or used as a pharmaceutically acceptable salt. In therapeutic compositions containing BA-1076 or a pharmaceutically acceptable salts thereof, BA-1076 or a pharmaceutically acceptable salt thereof is stereochemically enriched (e.g., BA-1049 or a pharmaceutically acceptable salt thereof is present in at least 10% ee, at least 50% ee, at least 75% ee, at least 80% ee, at least 90% ee, at least 95% ee, or at least 98% ee). Preferably, BA-1076 or a pharmaceutically acceptable salt thereof is present in at least 90% ee. More preferably, BA-1076 or a pharmaceutically acceptable salt thereof is present in at least 95% ee.

The term "BA-2017," as used herein, refers to a compound of formula:

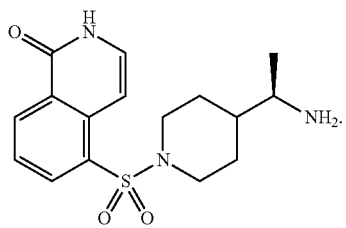 [SMILES: C[C@@H](N)C1CCN(S(=O)(=O)c2cccc3c(=O)[nH]ccc23)CC1]

In some embodiments, BA-2017 may be formulated and/or used as a pharmaceutically acceptable salt. In some embodiments, BA-2017 may be formulated and/or used as a pharmaceutically acceptable salt. In therapeutic compositions containing BA-2017 or a pharmaceutically acceptable salts thereof, BA-2017 or a pharmaceutically acceptable salt thereof is stereochemically enriched (e.g., BA-2017 or a pharmaceutically acceptable salt thereof is present in at least 10% ee, at least 50% ee, at least 75% ee, at least 80% ee, at least 90% ee, at least 95% ee, or at least 98% ee). Preferably, BA-2017 or a pharmaceutically acceptable salt thereof is present in at least 90% ee. More preferably, BA-2017 or a pharmaceutically acceptable salt thereof is present in at least 95% ee.

The term "BA-2057," as used herein, refers to a compound of formula:

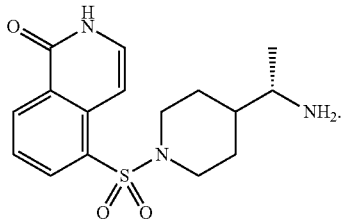 [SMILES: C[C@H](N)C1CCN(S(=O)(=O)c2cccc3c(=O)[nH]ccc23)CC1]

In some embodiments, BA-2057 may be formulated and/or used as a pharmaceutically acceptable salt. In some embodiments, BA-2057 may be formulated and/or used as a pharmaceutically acceptable salt. In therapeutic compositions containing BA-2057 or a pharmaceutically acceptable salts thereof, BA-2057 or a pharmaceutically acceptable salt thereof is stereochemically enriched (e.g., BA-2057 or a pharmaceutically acceptable salt thereof is present in at least 10% ee, at least 50% ee, at least 75% ee, at least 80% ee, at least 90% ee, at least 95% ee, or at least 98% ee). Preferably, BA-2057 or a pharmaceutically acceptable salt thereof is present in at least 90% ee. More preferably, BA-2057 or a pharmaceutically acceptable salt thereof is present in at least 95% ee.

The term "enantiomeric excess," as used herein, refers to an art-recognized measure of the proportion of enantiomers in a composition. Enantiomeric excess is measured in % ee. Percentage (%) ee can be calculated using the following formula.

$$(\%)ee = \frac{(C_{major} - C_{minor})}{(C_{major} + C_{minor})} \cdot 100\%,$$

where $C_{major}$ is a molar concentration of the major enantiomer in a composition, and $C_{minor}$ is a molar concentration of the minor enantiomer in the same composition. A composition is enantiomerically enriched, if (%) ee is greater than 0. A composition is racemic, if (%) ee is equal to 0.

The term "IOP-lowering prostaglandin," as used herein, refers to the biologically active metabolites of arachidonic acid and their analogs that are commonly used to reduce IOP because of their effectiveness. IOP-lowering prostaglandins are known in the art. Non-limiting examples of IOP-lowering prostaglandins include Travaprost (e.g., TRAVATAN®), Bimatoprost (e.g., LUMIGAN®), Latanoprost (e.g., XALATAN®), and Tafluprost (e.g., ZIOPTAN®).

The term "pharmaceutically acceptable salt," as used herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like.

The term "subject," as used herein, represents a human or non-human animal (e.g., a mammal) that is suffering from a disease (e.g., glaucoma, retinitis pigmentosa, macular degeneration, retinal angiogenesis, Alzheimer's Disease, Parkinson's Disease, ALS, stroke, or spinal cord injury) or is at risk of a disease (e.g., glaucoma, retinitis pigmentosa, macular degeneration, retinal angiogenesis, Alzheimer's Disease, Parkinson's Disease, ALS, stroke, or spinal cord injury), as determined by a qualified professional (e.g., a doctor or a nurse practitioner) with or without known in the art laboratory test(s) of sample(s) from the patient.

The terms "treating" or "treat," as used herein, refers to a therapeutic treatment of a disease (e.g., glaucoma, retinitis pigmentosa, macular degeneration, retinal angiogenesis, corneal blindness, Fuchs' corneal dystrophy, corneal scarring, Alzheimer's Disease, Parkinson's Disease, ALS, stroke, or spinal cord injury) in a subject. In some embodiments, a therapeutic treatment may slow the progression of the disease (e.g., glaucoma, retinitis pigmentosa, macular degeneration, retinal angiogenesis, corneal blindness, Fuchs' corneal dystrophy, corneal scarring, Alzheimer's Disease, Parkinson's Disease, ALS, stroke, or spinal cord injury), improve the individual's outcome, and/or eliminate the disease (e.g., glaucoma, retinitis pigmentosa, macular degeneration, retinal angiogenesis, corneal blindness, Fuchs' corneal dystrophy, corneal scarring, Alzheimer's Disease, Parkinson's Disease, ALS, stroke, or spinal cord injury). In some embodiments, a therapeutic treatment of a disease (e.g., glaucoma, retinitis pigmentosa, macular degeneration, retinal angiogenesis, corneal blindness, Fuchs' corneal dystrophy, corneal scarring, Alzheimer's Disease, Parkinson's Disease, ALS, stroke, or spinal cord injury) in a subject may alleviate or ameliorate one or more symptoms or conditions associated with the disease (e.g., glaucoma, retinitis pigmentosa, macular degeneration, retinal angiogenesis, Alzheimer's Disease, Parkinson's Disease, ALS, stroke, or spinal cord injury), diminish the extent of the disease (e.g., glaucoma, retinitis pigmentosa, macular degeneration, retinal angiogenesis, corneal blindness, Fuchs' corneal dystrophy, corneal scarring, Alzheimer's Disease, Parkinson's Disease, ALS, stroke, or spinal cord injury), stabilize (i.e., not worsening) the state of the disease (e.g., glaucoma, retinitis pigmentosa, macular degeneration, retinal angiogenesis, corneal blindness, Fuchs' corneal dystrophy, corneal scarring, Alzheimer's Disease, ALS, stroke, or spinal cord injury), and/or delay or slow the progress of the disease (e.g., glaucoma, retinitis pigmentosa, macular degeneration, retinal angiogenesis, corneal blindness, Fuchs' corneal dystrophy, corneal scarring, Alzheimer's Disease, Parkinson's Disease, ALS, stroke, or spinal cord injury), as compared to the state and/or the condition of the disease (e.g., glaucoma, retinitis pigmentosa, macular degeneration, retinal angiogenesis, corneal blindness, Fuchs' corneal dystrophy, corneal scarring, Alzheimer's Disease, Parkinson's Disease, ALS, stroke, or spinal cord injury) in the absence of therapeutic treatment.

BRIEF DESCRIPTION OF THE DRAWINGS

The foregoing and other objects of the present disclosure, the various features thereof, as well as the disclosure itself may be more fully understood from the following description, when read together with the accompanying drawings in which:

FIG. 5A is an image of an immunoblot showing the dose response for ROCK inactivation om human trabecular meshwork cells incubated at predetermined concentrations of BA-1076 or BA-2057. pMLC is a biomarker of ROCK activation and GAPDH an internal loading control;

FIG. 5B is an image of an immunoblot showing the dose response for ROCK inactivation in human trabecular meshwork cells incubated at predetermined concentrations of BA-2057 or a combination of BA-1076 and BA-2057. pMLC is a biomarker of ROCK activation and GAPDH an internal loading control;

FIGS. 8A and 8B are photomicrographs of adult rat optic nerve sections showing RGC regeneration after treatment with a ROCK inhibitor. The rat optic nerves were crushed and treated with 5 µL of 100 µM BA-1049 or vehicle (1×PBS) injected in the vitreous. Axons anterogradely labelled with CTB 2 weeks later extend past the crush (*). The top photo shows an optic nerve after injection with vehicle control, the bottom shows an optic nerve after treatment with BA-1049;

DETAILED DESCRIPTION

Figure 1:
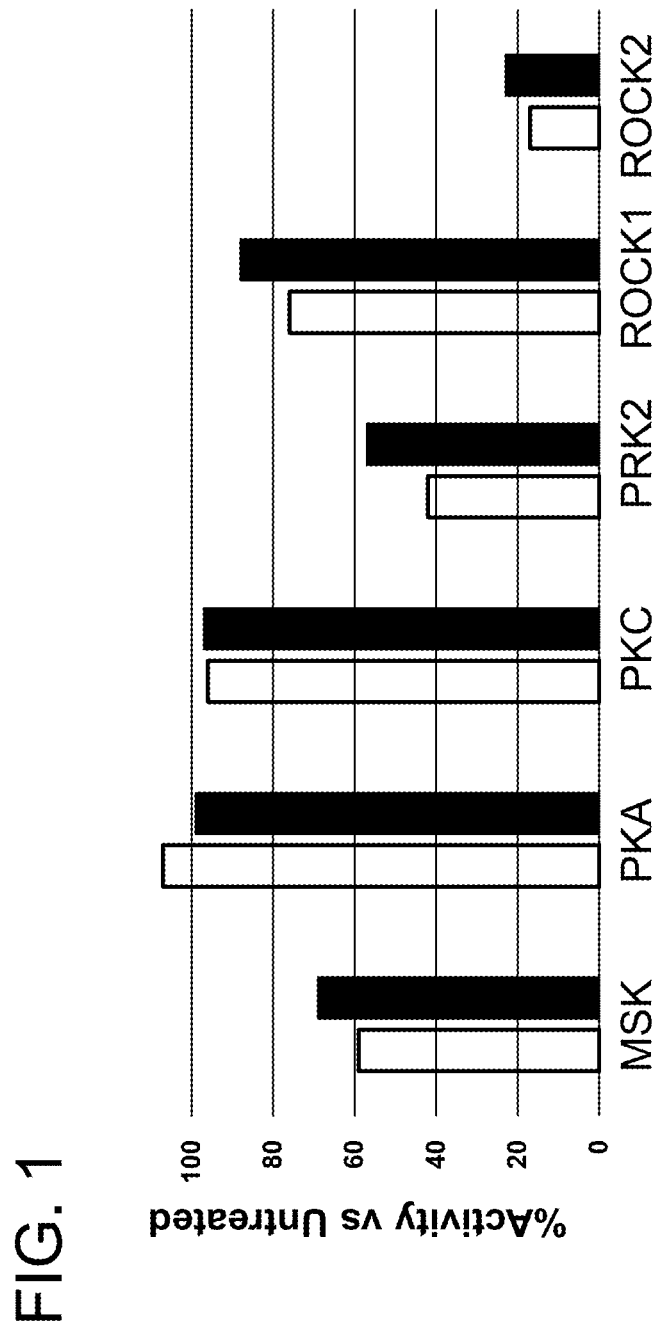
FIG. 1 is a graphic representation of the inhibitor profile of key kinases. Kinases identified in a primary screen with racemic API were re-tested with 10 µM BA-1076 (closed bars) and BA-1049 (open bars)
Figure 2A:
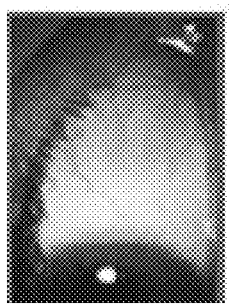
FIGS. 2A, 2B, 2C, and 2D are photographic representations of hyperemia in the human eye. The photographs show normal (FIG. 2A), mild (FIG. 2B), medium (FIG. 2C), and severe (FIG. 2D) hyperemia (from www.aeriepharma.com)
Figure 2B:
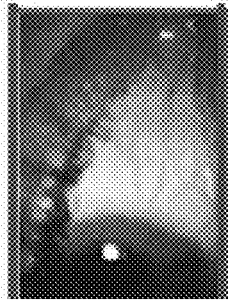
Figure 2C:
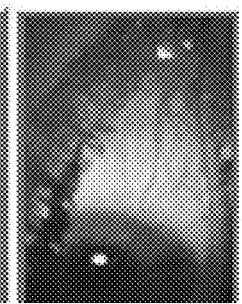
Figure 2D:
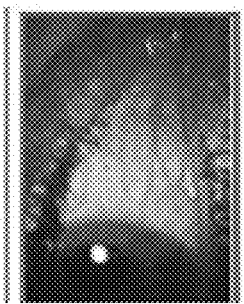

The disclosures of cited herein patents, patent application publications, and non-patent publications are hereby incorporated by reference in their entirety in order to more fully describe the state of the art as known to those skilled in the art as of the date of the invention described and claimed herein. The instant disclosure will govern in the instance that there is any inconsistency between the patents, patent applications, and publications and this disclosure.

Unless defined otherwise, all technical and scientific terms used herein have the same meaning as commonly understood by one of ordinary skill in the art to which this disclosure belongs. The initial definition provided for a group or term herein applies to that group or term throughout the present specification individually or as part of another group, unless otherwise indicated.

Disclosed are therapeutic compositions including a therapeutically effective amount of a compound of formula:

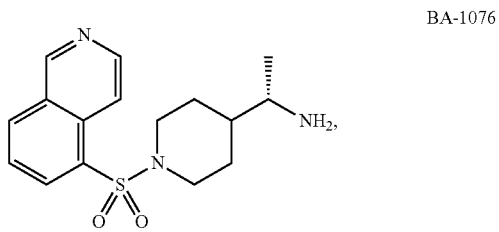 [SMILES: C[C@H](N)C1CCN(S(=O)(=O)c2cccc3cnccc23)CC1]

BA-1076 or a pharmaceutically acceptable salt thereof, where BA-1076 or a pharmaceutically acceptable salt thereof is stereochemically enriched (e.g., BA-1076 or a pharmaceutically acceptable salt thereof is present in at least 10% ee, at least 50% ee, at least 75% ee, at least 80% ee, at least 90% ee, at least 95% ee, or at least 98% ee). Preferably, BA-1076 or a pharmaceutically acceptable salt thereof is present in at least 90% ee. More preferably, BA-1076 or a pharmaceutically acceptable salt thereof is present in at least 95% ee.

Also disclosed are therapeutic compositions including a therapeutically effective amount of a compound of formula:

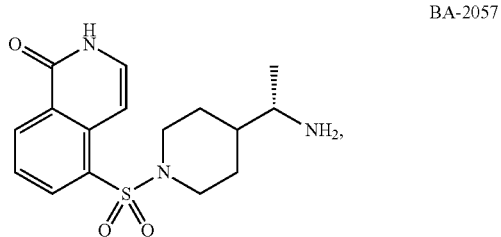 [SMILES: C[C@H](N)C1CCN(S(=O)(=O)c2cccc3c(=O)[nH]ccc23)CC1]

BA-2057 or a pharmaceutically acceptable salt thereof, where BA-2057 or a pharmaceutically acceptable salt thereof is stereochemically enriched (e.g., BA-2057 or a pharmaceutically acceptable salt thereof is present in at least 10% ee, at least 50% ee, at least 75% ee, at least 80% ee, at least 90% ee, at least 95% ee, or at least 98% ee). Preferably, BA-2057 or a pharmaceutically acceptable salt thereof is present in at least 90% ee. More preferably, BA-2057 or a pharmaceutically acceptable salt thereof is present in at least 95% ee.

Surprisingly, BA-1076 was found to inhibit ROCK2 selectively relative to ROCK1 (see Example 16). Inhibition of ROCK2 is advantageous in the treatment of eye disorders. Advantageously, neither BA-1076 nor its metabolite, BA-2057, exhibits off-target inhibition of GRK1, a rhodopsin kinase involved in phosphorylation of rhodopsin in mammalian rod cells. In contrast, BA-1049 is metabolized in vivo to BA-2017, which was found to target GRK1. Accordingly, unlike BA-1049 or BA-2017, BA-1076 and BA-2057 may be suitable for the development as a medicament for ophthalmic applications.

Methods of the Invention

Without wishing to be bound by theory, ROCK2 is believed to be active in injured RGCs and in glaucoma (Goldhagen et al. 2012 J Glau. 21(8): p. 530-538). ROCK may regulate deposition of extracellular matrix in the TM, and ROCK inhibitors may prevent ongoing reduction of aqueous outflow by this pathway (Pattabiraman et al. 2010 Amer J Physiol Cell Physiol. 298(3): p. C749-C763., Pattabiraman et al. 2014 J Cell Physiol. 229(7): p. 927-942). Inhibition of ROCK2 also acts on neurons and simulates plasticity and regeneration. Inhibition of ROCK may stimulate RGC regeneration in the optic nerve (Shaw et al. 2016 Exper Eye Res. 158: p. 33-42). Loss of dendritic connectivity may be one of the earliest event in glaucoma (El-Danaf et al. 2015 J Neurosci. 35(6): pm. 2329-2343), and ROCK inhibitors may stimulate plasticity and connections of dendrites.

The invention provides methods of treating a subject in need thereof, e.g., a subject suffering from glaucoma, retinitis pigmentosa, macular degeneration, retinal angiogenesis, corneal blindness, Fuchs' corneal dystrophy, corneal scarring, Alzheimer's Disease, Parkinson's Disease, ALS, stroke, or spinal cord injury. The invention also provides a method of reducing post-operative corneal scarring (e.g., post-glaucoma surgery corneal scarring). The methods of the invention include administering to the subject in need thereof a therapeutically effective amount of the therapeutic composition of the invention (e.g., a therapeutic composition including BA-1076, or a pharmaceutically acceptable salt thereof, and/or BA-2057 or a pharmaceutically acceptable salt thereof).

The present disclosure also provides a combination therapy (e.g., a ROCK2 inhibitor (e.g., BA-1076 or BA-2057) in combination with an IOP-lowering prostaglandin (e.g., latanoprost)) for treatment of glaucoma, retinitis pigmentosa, macular degeneration, and retinal angiogenesis and long-term compliance. Existing drugs successfully control IOP, and ROCK inhibition and treatment with latanoprost is synergistic in human glaucoma patients (Lewis et al. 2015 Brit J Ophthalmol. 100(3): p. 339-344, Inazaki et al. 2016 J Glau. 26(2): p. 96-100). A combination therapy is described that eliminates or reduces the side effect of hyperemia, while improving the efficacy of outflow through the TM and maintenance of RGC health while having higher efficacy in reducing IOP. The dose to impact TM cells and fibrosis may be lower than that required to lower IOP, and the dose to retain RGC health, as determined by dendritic arborisation, is less than needed for neuroprotection and/or regeneration in the optic nerve.

The combination treatment utilizes a drug that has minimal side effects to maximize patient compliance and show long-term benefit in slowing progression of disease.

Assessment of a compound in the treatment of glaucoma may be performed in a clinical trial. For example, a glaucoma treatment clinical trial may include a primary outcome of IOP lowering and secondary outcome of lack of hyperemia. The same patient population is followed for a longer period of time post-approval to investigate reduction of visual loss. The present combination therapy allows this approach because both dose and off-target effects contribute to hyperemia.

Figure 7:
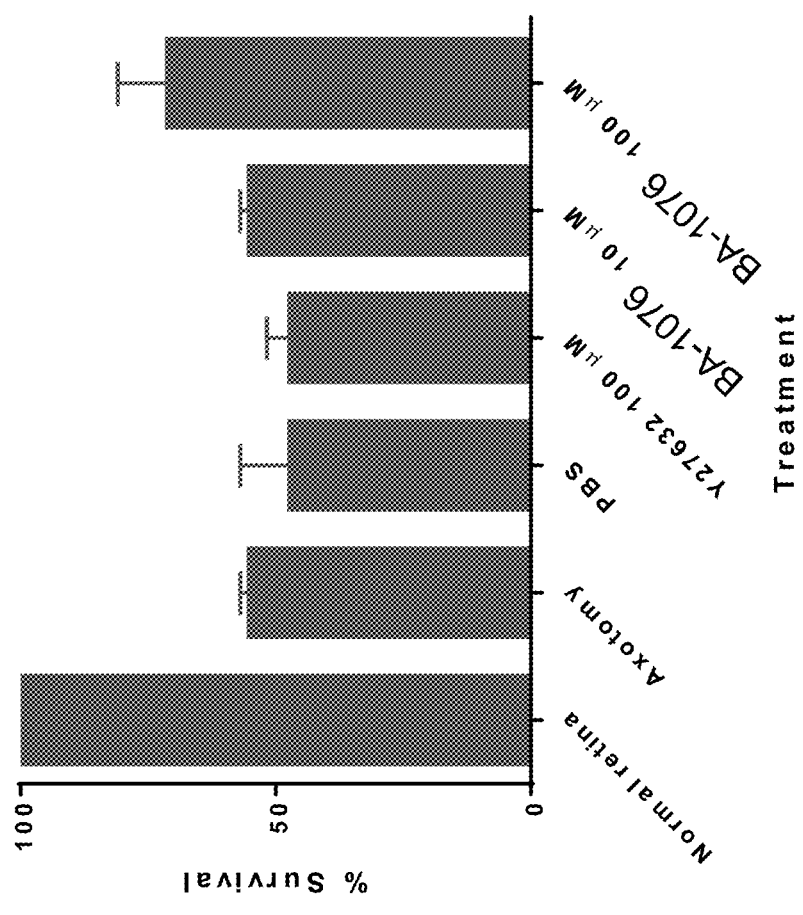
FIG. 7 is a graph showing the neuroprotection of test compounds one week after optic nerve cut. RGCs were retrogradely labelled with Fluorogold and counted in retinal whole mounts. Counts of normal (uninjured) retina are compared with axotomy alone, PBS injection control, Y-27632 as a comparator ROCK inhibitor, BA-1076 (racemic) at two different concentrations. Values shown are means±SEM, n=3-8 animals per group.

Without wishing to be bound by theory, therapeutic compositions of the invention may slow the progression of glaucoma, retinitis pigmentosa, macular degeneration, and retinal angiogenesis because they act on the TM, act on RGCs, and there is genetic proof of concept that they are a relevant molecular target in glaucoma (Whitlock et al. 2009 J Ocul Pharmacol Ther. 25(3): p. 187-194). Rho kinases are serine/threonine kinases that regulate actin/myosin networks within cells. ROCK phosphorylated proteins directly affect the contractility of the TM and its outflow properties, and they also regulate the synthesis and deposition of ECM in the TM (Pattabiraman et al. 2016 Eur J Pharmacol. 787: p. 32-42) ROCK inhibitors promote RGC regeneration, protection and plasticity (Chang et al. 2012 Ophthalmol. 119(5): p. 979-986, Shaw et al. 2016 Exper Eye Res. 158: p. 33-42). ROCK inhibition promotes RGC axon regeneration and protection in vitro and in vivo a finding now reproduced in many independent labs with Y-27632 and different inhibitors (Shaw et al. 2016 Exper Eye Res. 158: p. 33-42, Bertrand et al. 2005 J Neurosci. 25(5): p. 1113-21, Sagawa et al. 2007 Exper Neurol. 205(1): 9. 230-240) Inhibition of ROCK may maintain dendritic plasticity in various neurodegenerative diseases, a process which may be most achievable in the earliest stages of eye disorders. Inhibition of ROCK is neuroprotective (Shaw et al. 2006 Exper Eye Res. 158: p. 33-42) (FIG. 7). Reversing RGC degeneration at the earlies stage of the process may be more achievable than neuroprotection when RGCs are rapidly dying. ROCK inhibitors may stop VEGF-induced angiogenesis in both macular degeneration and diabetic retinopathy (van Niew Amerongen et al. 2003 Arterioscler. Thromb. Vasc. Biol. 23:211-217)

Therapeutic Compositions

Pharmaceutical formulation is a well-established art, and is described, e.g., in Gennaro (ed.), Remington. The Science and Practice of Pharmacy, 20th ed., Lippincott, Williams & Wilkins (2000) (ISBN: 0683306472); Ansel et al., Pharmaceutical Dosage Forms and Drug Delivery Systems, 7th ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

As a therapeutic composition, the ROCK inhibitor compounds can be mixed with a suitable amount of pharmacologically acceptable solvent or carrier which are standard in the art for creating topical eye drops so that to have the appropriate form for administration to a patient. The term "solvent" relates to diluent, auxiliary medicinal substance, f or carrier which is mixed with the ROCK inhibitor(s) for administration to a patient. Similarly, the term "pharmaceutically-acceptable carrier" includes any and all solvents, excipients, antibacterial and antifungal agents, and solutions used in the art to formulate drugs to be applied as eye drops. The composition can include a pharmaceutically-acceptable salt (See e.g., Berge et al. (1977) *J. Pharm. Sci.* 66:1-19).

Application of the therapeuticcompositions of the present invention can be both local and/or systemic. For treatment of eye disease, topical treatment as eye drop is effective. Other administration methods comprise enteral such as oral, sublingual and rectal; local such as intraocular, oculo-dermal, through-dermal, and intradermal; and parenteral. Acceptable parenteral methods of administration comprise injections, for example, intravenous, intramuscular, hypodermic injections et cetera, and non-injection methods. Per ocular or per oral administration of the compounds and the therapeutic compositions of the present invention is useful. More specifically, the administration can be carried out in the form of capsules, tablets, pills, pillets, granules, syrups, elixirs, solutions, ophthalmologic solutions, suspensions, emulsions, or retarded-release substances, or in any other form suitable for administration to a patient.

A therapeutically-effective amount of the therapeutic composition of the invention required for treatment of glaucoma or related disorder depends on the severity of the disorder or symptom thereof. The method of administration may be determined at consultation with a physician such as an ophthalmologist in charge. In principle, topical solutions range from 0.001% to 5% (w/v) solution. The eye drops can be applied once daily or up to 3 times daily. For oral dosing, acceptable doses may be, e.g., from 0.001 mg/kg to 10 mg/kg of a subject's body weight.

A therapeutically-effective amount of prostaglandin or prostaglandin analog is the same as the approved range (0.005% (w/v)) or 10-fold lower (0.0005% (w/v)); ranges for other drugs are the same as the FDA-approved range or 10-fold lower.

EXAMPLE 1

Selection of BA-1076 and BA-2057

ROCK inhibitors are neuroprotective for RGCs in different models of RGC injury, and they promote axon regeneration in the optic nerve of adult rats after optic nerve crush (Bertrand et al. 2005 J Neurosci. 25(5): p. 1113-21, Lehmann et al. 1999 J Neurosci. 19(17): p. 7537) One of the earliest changes in glaucoma may be the loss of RGC connections, both in the retina (El-Danaf et al. 2015 J Neurosci. 35(6): p. 2329-2343, Binley et al. 2016 Eur J Neurosci. 44(3): p. 2028-2039) and target areas of the brain (Crish et al. 2010 Proc Natl Acad Sci. 107(11): p. 5196-5201). Neuronal connectivity is important for RGCs survival and stimulating regenerative plasticity may be an achievable short-term goal by acting on RGCs before substantial connection is lost. Once substantial apoptosis has set in, the process of degeneration may be more difficult to reverse. The present method restores usable visual function by regeneration of RGC axons and re-establishing neural connections in the eye and visual system.

Molecular modeling and rational drug design were used to create and screen over 50 ROCK inhibitors. These ROCK inhibitors were screened for selectivity for ROCK2 and ability to promote neurite outgrowth. Several lead inhibitors came out of this screen and further screened for inhibition of key AGC class kinases by a single dose inhibition assay performed with 10 µM active pharmaceutical ingredient (API). The lead compound is chiral. The R and S enantiomers are BA-1049 and BA-1076, respectively. They have different selectivity for ROCK2 (Table 2) and different off-target profiles (Table 1; FIG. 1). Neither compound inhibited PKA, thereby differentiating them from other ROCK inhibitors in development (FIG. 1).

Figure 13:
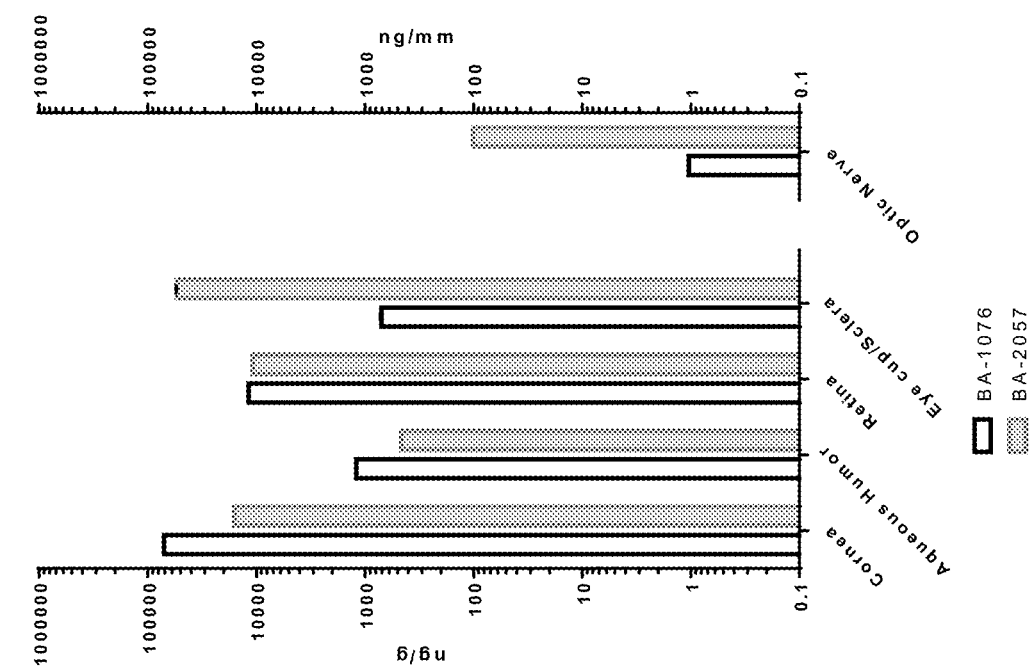
FIG. 13 is a graph showing the exposure levels of BA-1076 and its metabolite BA-2057 after topical application of a 5% solution to the eye.

A major metabolite of BA-1049, termed BA-2017, is made in vivo (see US 2017/0313680). BA-2017 was synthesized and determined to have a cleaner off-target profile than BA-1049 (Table 1). BA-1076 is also metabolized in vivo to BA-2057. This was demonstrated by applying BA-1076 topically to rat eyes and observing the formation of the metabolite in vivo, as detected by LCMS of collected tissue samples (FIG. 13).

TABLE 1

DiscoverX Kinome screen. Immobilized kinase substrates are incubated with DNA-tagged kinase domains tagged plus API; results are expressed as % of control

| Tests performed at the CRO | Kinase or transporter | 10,000 nM API | | | | 500 nM API Netarsudil |
|---|---|---|---|---|---|---|
| | | BA-2017 | BA-1049 | BA-1076 | BA-2057 | |
| # Hits | <10% binding | 7 | 11 | 7 | 2 | 11 |
| Kinome Screen % inhibition | ROCK1 | >99 | >99 | >99 | >98 | 93 |
| | ROCK2 | >99 | >99 | >99 | >96 | 93 |
| | PKC ε | 94.7 | 95 | 86 | <70 | 93 |
| | PKC Δ | <85 | <70 | <70 | <70 | 91 |
| | Other | GRK1 | none | (ABL) | none | Not known |
| Safety Screen % inhibition | NET | none | none | none | none | 96 |
| | SERT | none | none | none | none | 94 |

A 468-target kinome screen and a safety screen were carried out to examine the off-target profiles of different kinase inhibitors (DiscoverX, Freemont, Calif.). The kinome screen is a binding assay where API interference of kinase domain/substrate binding is assessed as percent of control. Less than 10% binding (or >90% binding inhibition) is most biologically relevant and considered as a 'hit'. BA-2017 only had 7 off-target hits compared to BA-1049 and Netarsudil, which both had 11 hits (Table 1) (Studirvant et al. 2016 Bioorg Med Chem Lett. 26(10):2475-2480). BA-1076 also showed 7 off-target hits, while its active metabolite BA-2057 showed the cleanest off-target hit profile with only two hits, which were the target kinases ROCK1 and ROCK2. Published data for Netarsudil were with 200 times less API. Netarsudil also inhibits both norepinephrine transporter (NET) and serotonin transporter (SERT) (Kopczynski et al. 2012 Invest Opthalmol Vis Sci. 53(14): p. 5080-5080; Studirvant et al. 2016 Bioorg Med Chem Lett. 26(10):2475-2480). The NET activity likely helps to decrease IOP but might increase hyperemia, while the SERT activity might have long-term safety consequences (Costagliola et al. 2004 CNS drugs 18(8): p. 475-484).

BA-2017 was found to have the highest affinity for ROCK2 (Table 2). The data in Table 2 were obtained at ATP concentration below those corresponding to Km.

TABLE 2

| Compound | IC50 (µM) determined at 10 µM ATP** | | |
|---|---|---|---|
| | ROCK2 | ROCK1 | Fold-difference |
| BA-1076 | 0.73 | 10 | 14 |
| BA-1049 | 0.24 | 3.9 | 16 |
| BA-2017 | 0.05* | nd | nd |
| BA-2057 | nd | nd | nd |

*preliminary;
nd = not done**

A common off-target effect of ROCK inhibitors is inhibition of PKA because the ATP-binding pocket of ROCK and PKA are highly conserved (Green et al. 2015 J Med Chem. 58(12): p. 5028-5037). Y-27632, Fasudil, hydroxyfasudil all bind PKA, and Fasudil binds ROCK and PKA with same affinity (Jacobs et al. 2006 J Biol Chem. 281(1): p. 260-268). Ripasudil and Netarsudil both inhibit PKA, PKC and CaMKII (Isobe et al. 2014 Curr Eye Res. 39(8): p. 813-822; Lin et al. 2018 J Ocul Pharmacol Ther. 34(1-2): 40-51). Efficacy and side effects of ROCK inhibitors are determined by multiple parameters that include ability to penetrate the cornea, metabolism, off-target effects, and therefore, in vivo studies are key to assess safety.

Oral dosing of 4 cynomolgus monkeys dosed with 18 mg/kg oral BA-1049 by oral gavage were completed to understand potential systemic side effects. The only side effects noticed at this dose was squinting by the monkeys. BA-1049 has some activity toward G-protein couple protein kinase1, a kinase involved in sensitivity to light and defects in GRK1 are known to cause Oguchi disease 2 (Orban et al. 2016 G Protein-Couple Receptor Kinases p. 25-43). By contrast, BA-1076 does not have this off-target effect. Therefore, this surprising finding shows that BA-1049 is not suitable for development for treatment of ophthalmological disease, whereas BA-1076 has an appropriate activity and safety profile.

Given the selectivity of BA-1076 and BA-2057 for ROCK2, and the lack of inhibition of kinases important for retinal function, BA-1076 and BA-2057 were selected as compounds useful for treatment of ophthalmological disorders.

EXAMPLE 2

Conjunctival Hyperemia

A side effect of topical drugs that cause vasodilation is conjunctival hyperemia. Hyperemia is a serious issue for daily use and compliance for treatment of glaucoma. Patients object to daily red eyes, and progression of glaucoma is slow and painless so it is easy to skip daily dosing. Hyperemia with current ROCK inhibitors is much higher than with prostaglandins: >50% of treated patients had hyperemia in the Netarsudil and Ripasudil clinical studies (Bacharach et al. 2015 Opthalmology 122(2): p. 302-307, Lewis et al. 2015 Brit J Opthalomo. 100(3): p. 339-344, Tanihara et al. 2013 Amer J Ophthalmol. 156(4): p. 731-736 e2, Tanihara et al. 2016 Acta Ophthalmol. 94(1): p. e26-e34, Levy et al. 2015 Amer J Ophthalmol. 159(5): p. 980-958 e1, Tanihara et al. 2013 JAMA Ophthalmol. 131 (10): p. 1288-1295). BA-1076 did not cause hyperemia on daily repeat dose study with Dutch Belted rabbits (Absorption Biosciences) whereas Netarsudil caused 4-8 hours of mild hyperemia in Dutch belted rabbits (Kopczynski et al. 2012 Invest Opthalmol Vis Sci. 53(14): p. 5080). Hyperemia of Ripasudil is more frequent and of longer duration than Netarsudil in human clinical studies (Bacharach et al. 2015 Opthalmology 122(2): p. 302-307, Tanihara et al. 2013 Amer J Ophthalmol. 156(4): p. 731-736 e2)

To test for hyperemia, the rabbit is a standard species used in ocular tolerability studies based upon historical data and FDA requirements. For this study, four (4) Dutch-Belted rabbits (*Oryctolagus cuniculus*) were manually restrained to facilitate topical dosing followed by ocular examinations, and IOP measurements. Prior to placement on study, each animal underwent an ophthalmic examination (slit-lamp biomicroscopy, indirect ophthalmoscopy). Ocular findings were scored according to a modified McDonald-Shadduck Scoring System. BA-1076 (racemic) or control article were administered to the animals once daily into both eyes starting on Day 1. Test and control articles were dosed in the morning at approximately the same time every day (~8 am±2 hours). Animals were observed within their cages once daily throughout the study period. Animals were observed for changes in general appearance and behavior. Any abnormal observation was reported to the Study Director. Ocular findings were scored according to a modified McDonald-Shadduck Scoring System. The scoring system 0=normal and numbers of 1-4 score mild to severe.

As shown in Table 3, none of the animals treated with racemic BA-1076 showed any adverse ocular findings.

TABLE 3

| Hyperemia testing in Dutch-Belted rabbits - Results at Day 3 | | | | | | | | |
|---|---|---|---|---|---|---|---|---|
| | Vehicle Rabbit 1 | | Vehicle Rabbit 2 | | BA-1076 Rabbit 1 | | BA-1076 Rabbit 2 | |
| Eye | OD | OS | OD | OD | OS | OD | OS | OS |
| Conjunctival Discharge | 0 | 0 | 0 | 0 | 0 | 0 | 0 | 0 |
| Conjunctival Congestion | 0 | 0 | 0 | 0 | 0 | 0 | 0 | 0 |
| Conjunctival Swelling | 0 | 0 | 0 | 0 | 0 | 0 | 0 | 0 |
| Cornea | 0 | 0 | 0 | 0 | 0 | 0 | 0 | 0 |
| Surface Area of Cornea Involvement | 0 | 0 | 0 | 0 | 0 | 0 | 0 | 0 |
| Pannus | 0 | 0 | 0 | 0 | 0 | 0 | 0 | 0 |
| Pupillary Response | 0 | 0 | 0 | 0 | 0 | 0 | 0 | 0 |
| Aqueous Flare | 0 | 0 | 0 | 0 | 0 | 0 | 0 | 0 |
| Cellular Flare | 0 | 0 | 0 | 0 | 0 | 0 | 0 | 0 |
| Iris Involvement | 0 | 0 | 0 | 0 | 0 | 0 | 0 | 0 |

FIG. 2A through FIG. 2D are representative of hyperemia in the human eye (from www.aeriepharma.com).

Hyperemia was not correlated with IOP-lowering in a screen of different ROCK inhibitors (Sturdivant et al. 2016 Bioorg Med Chem. 26(10): p. 2475-2480), and may be an off-target effect, or result from different ROCK1/ROCK2 affinity. Vascular endothelial cells in different tissues vary in ROCK1/ROCK2, and many ROCK inhibitors target the widely expressed PKA (Green et al. 2015 J Med Chem. 58(12): p. 5028-5037), a kinase with multiple roles in cellular homeostasis and response to extracellular signals. Abnormal activation of the Rho/ROCK pathway, such as occurs in glaucoma, unbalances the regulation of vascular tone. Blood flow in the eyes is regulated in large part by vasoactive substances (e.g., adenosine and bradykinin) and endothelial-derived nitric oxide-mediated vasodilation. Thus, multiple mechanisms may contribute to hyperemia.

BA-1076 (racemic) was screened for hyperemia in Dutch belted rabbits for three days of 1% topical dosing. Neither compound induced any detectable hyperemia. (Table 3). Thus, these ROCK inhibitors have promise for therapeutic use in treating eye pathologies.

Consistent with past trend to report only positive results, studies with DB rabbits that show IOP lowering by Ripasudil and Netarsudil did not report effects on hyperemia (Kaneko et al. 2016 Sci rep. 6: Article 19640, Kiel et al. 2014 Invest Ophthalmol Vis Sci. 55(13): p. 2900-2900). An ARVO poster available on-line shows that even low doses of Netarsudil (0.04%) caused hyperemia lasting at least 8 hours on day 1, and it is consistently seen over 10 days, decreases to mild (deLong et al. 2012 Invest. Ophthalmol. Vis. Sci. 53(14):3867).

EXAMPLE 3

Combination Therapies

The present disclosure describes a combination therapy including a ROCK inhibitor and a prostaglandin or prostaglandin analog. IOP-lowering prostaglandins are typically biologically active metabolites of arachidonic acid, or analogs of the metabolites, that are commonly used to reduce IOP. They can reduce IOP by 27% to 33% and require only once daily dosing. Such analogs include Travaprost (e.g., TRAVATAN®), Bimatoprost (e.g., LUMIGAN®), Latanoprost (e.g., XALATAN®), or Tafluprost (e.g., ZIOPTAN®). This therapy addresses ROCK targets of TM and RGCs, rather than an inhibitor that will compete with standard-of-care IOP lowering.

To determine the efficacy and safety of this combination therapy, the dose-response of a subject ROCK inhibitor, BA-1076, in combination with Latanoprost is investigated to achieve exposure of BA-1076 and its primary metabolite BA-2057 in the TM without hyperemia, by method described in example 2. Latanoprost is effective in IOP lowering, and acts synergistically with ROCK inhibitors (Lewis et al. 2015 Brit J Ophthalmol. 100(3): p. 339-344, Tanihara et al. 2015 JAMA Ophthalmol. 133(7): p. 755-761). By focusing on biology of TM, retina and therapeutic window, a combination drug achieves required IOP lowering while providing the benefits of ROCK inhibition, without the hyperemia.

Figure 3:
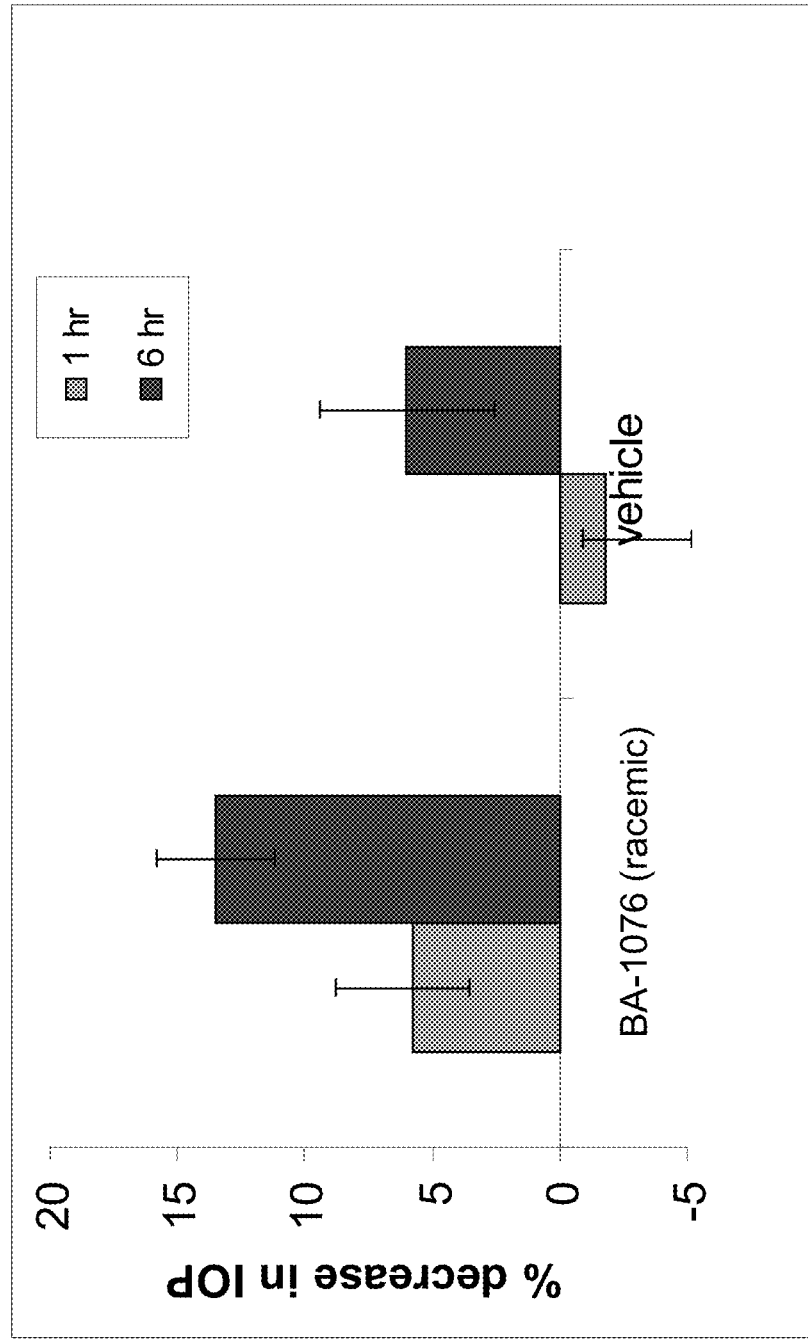
FIG. 3 is a graph showing intraocular pressure changes, following the treatment of hypertensive eyes of Cynomolgus monkey with BA-1076 (racemic) or vehicle. The IOP was measured after a single application of 1% BA-1076 (racemic, n=9) compared to untreated lasered eyes (n=7). Reduction in IOP was statistically significant.

A dose of 1% BA-1076 (racemic mixture) was an effective dose to lower IOP in a monkey model of glaucoma (FIG. 3). It is notable that there was no significant hyperemia in rabbits or monkeys in the study of IOP-lowering after topical instillation of BA-1076 (racemic).

EXAMPLE 4

Activity of Hydroxy Metabolite

Figure 4A:
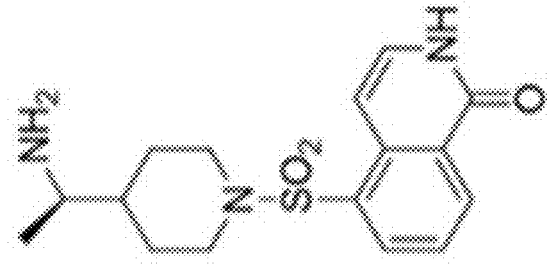
FIG. 4A is a scheme showing the structure of BA-1076.
Figure 4B:
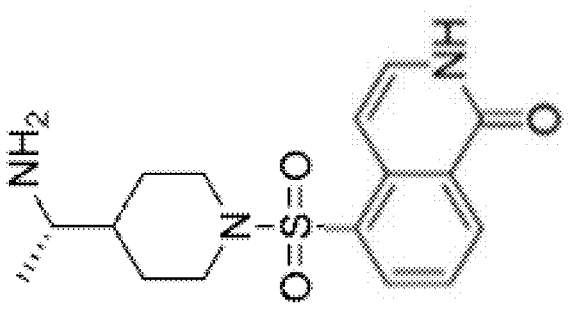
FIG. 4B is a scheme showing the structure of BA-1049.
Figure 4C:
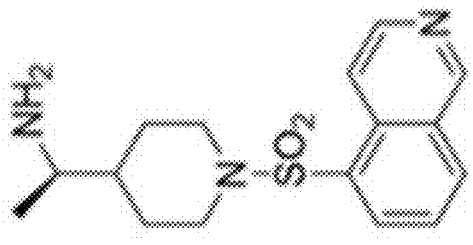
FIG. 4C is a scheme showing the structure of BA-2057.
Figure 4D:
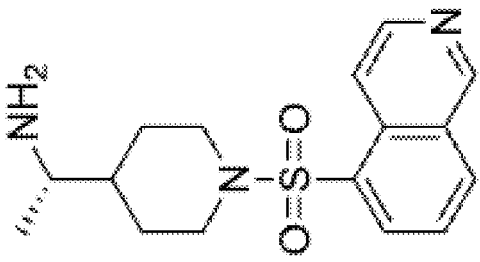
FIG. 4D is a scheme showing the structure of BA-2017.

The racemic mixture is composed from the enantiomers BA-1076 and BA-1049 whose structures are shown in FIG. 4A and FIG. 4B, respectively. These inhibitors have active metabolites, BA-2057 (FIG. 4C) and BA-2017 (FIG. 4D), respectively, which are enantiomers as well.

To form the active metabolites BA-2057 and BA-2017 an oxygen is added to the isoquinoline of the parent compounds BA-1076 or BA-1049, respectively. The isoquinoline is a structure in common with Ripasudil. It is likely that aldehyde oxidase (AO) converts the parent (BA-1076 or BA-1049) to the active metabolite (BA-2057 or BA-2017, respectively). AO is a cytosolic enzyme that has high expression in brain (Strolin Benedetti et al. 2006 Expert opi drug metab toxicol. 2(2): p. 895-921), superficial cornea and choroid-retina (Isobe et al. 2016 J Ocu Pharmacol Ther. 32(7): p. 405-414).

To examine the potency of BA-1076 an its active metabolite BA-2057 in disease-relevant cell-based assay, human trabecular meshwork (TM) cells were cultured and dose-response analysis were performed. Different concentrations of BA-1076, BA-2057 or a combination of both were tested.

To quantify the inhibitory effect of the compounds the TM cells were serum starved and treated for 1 hour with the indicated compound concentration and then lysed and extracted for SDS-PAGE and immunoblotting for phosphorylated myosin light chain kinase 2 (pMLC2), which is a biomarker for cellular ROCK activity.

These dose-response studies using BA-1076, the active metabolite BA-2057, or a combination of both on human trabecular meshwork cells in culture showed potency to reverse ROCK activation, with the metabolite BA-2057 was more potent than the parent BA-1076 and (FIG. 5). Combination of both parent and metabolite further increased potency.

EXAMPLE 5

Kinome Screening

Selectively to a broad menu of human kinases of BA-2017, BA-2057, BA-1049 and BA-1076 was tested using DiscoverX kinome screen (Table 1). In the kinome screen BA-2017 had fewer off-target hits (Table 1) than BA-1049. Importantly, BA-1049 showed binding to G-protein couple protein kinase1 (GRK1) (Table 1) one of 7 GRKs that phosphorylates rhodopsin and defects in GRK1 function are known to cause Oguchi disease Type 2. By contrast, BA-1076 does not have this off-target effect. An interesting hit from the kinome screen was on Abl (Table 1), an oncogene that also regulates many cellular activities, including vascular leakage. Although a second kinome screen did not confirm significant binding of BA-1076 to Abl, with a potential activity towards Abl, BA-1076 may have potential to treat retinal diseases with vascular involvement, such as neovascular glaucoma, diabetic macular edema, and age-related macular degeneration and be further efficacious in neurological disorders where both ROCK2 and Abl actively participate in development of disease including Alzheimer's disease and Parkinson's disease.

The data on off-target hits with the R enantiomer (BA-1049) and the S-enantiomer (BA-1076) that have different biological activity highlight the surprising finding that BA-1049 is not suitable for use for treatment of ophthalmological diseases because it also inactivates a key kinase required for photoreceptor sensitivity. The finding that BA-1076 inhibits ROCK2 and potentially Abl indicates the surprising finding that BA-1076 could be a suitable drug for treatment of neurological diseases where both kinases are abnormally activated, also because its primary metabolite BA-2057 showed an even cleaner off-target profile than BA-2017 (Table 1).

Effects of BA-1076, BA-2057, Ripasudil (Kowa), and Netarsudil (Aerie) on the stimulation of hyperemia in Dutch-Belted (DB) rabbits may be compared. The comparison may be for an acute hyperemia or chronic hyperemia, e.g., in long term studies.

A safety screen with BA-1076 and the active metabolite BA-2057 was completed to check potential agonistic or antagonistic off-target liability against a broad menu of human targets important for pharmaceutical safety profiling. These targets include GPCRs, transporters, ion channels, nuclear receptors, non-kinase enzymes. Of the 88 targets tested, no significant off target hits were detected that would confer safety risk.

EXAMPLE 6

Efficacy on IOP, Aqueous Humor Dynamics

For further testing BA-1076 and BA-2057, a monkey model is used because of similar AO metabolism to humans and similar eye structure.

A study with a racemic mixture of BA-1076 showed significant reduction of intraocular pressure in hypertensive Cynomolgus monkeys 1 hour and 6 hours after a single topical instillation; longer time points were not examined (FIG. 3). To further investigate dose and efficacy in Cynomolgus monkey, a single dose study is carried out with API alone or in combination with Latanoprost, and compared to latanoprost alone. Clinical studies show latanoprost acts synergistically with ROCK inhibitors. Aqueous humor flow and IOP are measured at baseline and 6 hours after dosing, a time chosen to allow comparison with published aqueous humor flow. Aqueous humor flow is measured with a scanning computerized fluorophotometer after applying fluorescein to the eye. The dosing is in combination with 0.005% Latanoprost, and four combination doses are tested, with 2 monkeys (4 eyes) in each group.

EXAMPLE 7

Efficacy for Reducing Fibrosis in Trabecular Meshwork (TM)

To investigate potential reduction of TM fibrosis by the API+Latanoprost, human TM cells are grown to confluency, and the effect on cell shape is assessed by actin staining. Fibrosis is characterized by an excessive deposition of extracellular matrix. To examine the efficacy of BA-1076 and BA-2057 on ECM deposition is examined by measuring the ECM protein fibronectin in TM cell lysates by immunoblotting after stimulation with transforming growth factor beta (TGFβ).

Activation of the canonical TGFβ pathway promotes ECM in cultured TM cells (Inoue-Mochita et al. 2015; PLoS One 10(3):e0120774) and TGFβ concentrations are elevated in glaucomatous eyes in humans (Agarwal et al., 2015; Molecular Vision 21:612-20). TM cells were first serum-starved for 24 hours and then treated with 2.5 ng/ml TGFβ and different concentrations (0, 1, 3, 10, 30, 100 μM, respectively) of either BA-1076 or BA-2057.

Figure 6A:
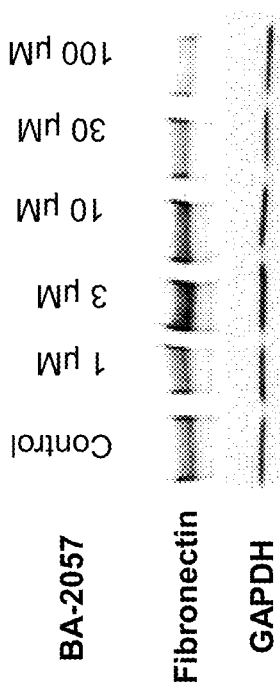
FIGS. 6A and 6B are images of immunoblots showing the dose response for ECM deposition in human trabecular meshwork cells incubated at predetermined concentrations of BA-1076 or BA-2057. Fibronectin was used is a biomarker of fibrosis and GAPDH an internal loading control.
Figure 6B:
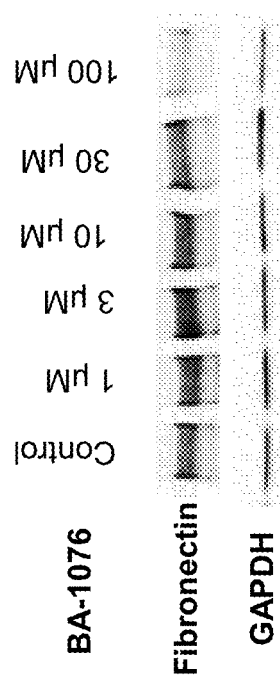

After 24 hours of treatment cells were lysed and processed and fibronectin in each sample was revealed by immunoblotting. Fibronectin levels decreased dose-dependently, with the most pronounced decrease in the combination of both drugs. Furthermore, BA-2057 was more potent in decreasing fibronectin deposition than BA-1076 (FIG. 6).

In addition, a combination therapy of API (either BA-1076 or BA-2057) and Latanoprost is tested and compared against latanoprost alone to determine if there are synergistic effects of the combination. Latanoprost increases ECM turnover in the TM and ciliary body through a different pathway than BA-1076/BA-2057 namely by increasing expression of matrix metalloproteinases (MMPs), which is not affected by treatment with BA-1076 and with treatment with BA-2057.

TM cells are treated with 2.5 ng/ml TGFβ and with 1 μM of latanoprost alone or a combination 1 latanoprost and API (either BA-1076 or BA-2057) for 24 hours. After 24 hours of treatment cells are lysed and processed and fibronectin in each sample is revealed by immunoblotting. Combination of latanoprost and either BA-1076, BA-2057 or a combination of both reduces fibronectin protein levels more strongly than latanoprost alone. The most pronounced decrease is observed in the combination of latanoprost, BA-1076 and BA-2057. Furthermore, Latanoprost and BA-2057 is more potent in decreasing fibronectin deposition than Latanoprost and BA-1076.

EXAMPLE 8

RGC Distal Axonopathy and Changes in RGC Cell Soma

An early hallmark of glaucoma in animal models are defects in axonal transport (Nickells et al. 2012 Ann Rev of Neurosci. 35: p. 153-179, Crish et al. 2010 Proc Natl Acad Sci. 107(11): p. 5196-5201). There is a decrease in slow axonal transport after optic nerve injury (McKeracher et al. 1990 J Neurosci. 10(8): p. 2834-2841) that coincides with a decrease in tubulin mRNA levels in RGC cell soma (McKerracher et al. 1993 J Neurosci. 13(6): p. 2617-2626). In addition, after optic nerve injury RGCs lose trophic responsiveness (Pernet et al. 2006 Brain. 129(Pt 4): p. 10147-26) and hence, even application of BDNF via viral delivery does not confer long-term RGC survival but only delays RGC cell death (Di Polo et al. 1998 Proc Natl Acad Sci USA. 95(7): p. 3978-83). Restoring axonal transport at the earliest phase of glaucoma has potential to reverse progress of the disease (Crish et al. 2010 Proc Natl Acad Sci. 107(11): p. 5196-5201). Axon constriction at the optic nerve head is a site of initial axon damage in glaucoma and is an early event preceding RGC cell death by apoptosis (Nickells et al. 2012 Ann Rev of Neurosci. 35: p. 153-179).

Animal models show that RGC death only occurs late in disease, and that there is a large window between RGC dysfunction and death (Chang et al. 2012 Ophthalmology. 119(5): p. 979-986). The different markers of RGC dysfunction are examined in a rat model of glaucoma where latex microspheres are injected into the anterior chamber of the eye to block outflow through the TM. In Sprague Dawley rat RGC loss is 20%-30% over a 4-6 weeks period when 20 μL of beads are injected weekly. This severe model is used to start to determine the amount of API in the retina 1 hour after topical installation of the API/latanoprost combination. Rats are topically dosed with API/Latanoprost for a week after microbead injection, a time when IOP is elevated. The right eyes serve as non-glaucomatous controls.

The beta-3 (BIII) isotype of tubulin is dramatically reduced in rat after optic nerve injury and increase when RGCs regenerate in PN grafts (Fournier et al. 1997 J Neurosci. 17(12): p. 4623-4632). BIII tubulin expression is decreased in RGCs in glaucoma (Soto et al. 2008 J Neurosci. 28(2): p. 548-561). Loss of BIII tubulin is a biomarker of early RGC degeneration. Ocular treatment with BA-1076 and BA-2057 prevents the loss of BIII tubulin immunostaining in glaucoma eyes in comparison to vehicle-treated eyes. BIII tubulin is observed in radial sections, and RGCs identified by labeling with Brin3. For quantitative comparisons, control and treated radial cryostat sections are cut in the same block and mounted on the same slide, and labeled together with BIII isotype-specific antibodies. This study reveals early changes in tubulin expression that correlate with decreased axonal transport, and demonstrate that ocular dosing with ROCK inhibitors can reverse this effect.

ROCK activation is examined in the same microbead model of glaucoma in rats 4 weeks after daily topical dosing in rats with left and right eyes injected with beads. API alone or API+Latanoprost are delivered once daily by 15 µL eye drop instilled into the left eyes (glaucoma/treated) and right eyes left untreated (glaucoma/untreated). Retinas and trabecular meshwork are prepared for Western blots and probed with p-cofilin and phospho myosin light chain (p-MLC), as biomarkers of ROCK2 activation. Retinas and TM deriving from untreated glaucoma eyes show high levels of ROCK activity as demonstrated by high protein levels phosphorylated cofilin and myosin light chain 2 (MLC2), both substrates of ROCK. By contrast, glaucoma eyes treated with BA-1076 and BA-2057 do not show elevated p-cofilin nor p-MLC2 levels demonstrating that ROCK activation is successfully inhibited.

EXAMPLE 9

Intraretinal Changes

In glaucoma, loss of RGC terminals may contribute to loss of retrograde transport and trophic support (Chang et al. 2012 Ophthalmology. 119(5): p. 979-986), and neurotrophic support is critical for RGC survival (Shen et al. 1999 Neuron. 23: p. 285-295). In the adult rat, retinal ganglion cells (RGCs) die rapidly when their axons are severed close to the optic disc (FIG. 7), but fewer RGC die when the nerve is cut further away (Villegas-Perez et al. 1993 J Neurobio. 24: p. 23-36). Thus, RGC cell death is not simply loss of target innervation, but a change of trophic responsiveness of RGCs after injury. Intraretinal connections are needed for RGC survival, and non-neuronal cells, such as neurotoxic astrocytes and macrophage factors, impact RGC health and survival.

To evaluate changes in the RGC dendritic arbor in glaucoma and the ability of the API to prevent neuronal loss in the retina, mice are used which carry an enhanced GFP (eGFP) driven by the Hb9 promoter (B6.Cg-Tg(Hlxb9-GFP) 1Tmj/J; Jackson Labs), which directs GFP expression to the on-off direction-sensitive ganglion cell (ooDSGC) subpopulation of retinal ganglion cells (Trenholm et al. 2011 Neuron. 71(4): p. 683-694). These mice allow visualization of non-overlapping RGCs for unambiguous identification of individual dendritic arbors. Treated and control glaucoma eyes are examined, as well as normal eyes 1 month after weekly microbead injection and daily eye drops. The eyes are fixed by perfusion and prepared for retinal whole mounts, and the labeled ganglion cells visualized by fluorescence microscopy. Images are imported into ImageJ and analyzed for dendritic field area (using the polygon tool to join points along the perimeter of the field) and subjected to Sholl analysis using the plugin for Image J to be able to characterize dendritic branching and complexity of normal, glaucoma/treated and glaucoma/control RGCs. Treatment with BA-1076 and BA-2057 protect and/or restore retinal ganglion cell dendritic arbors.

EXAMPLE 10

Neuroprotection

Intravitreal injection of 1% racemic BA-1076 after optic nerve cut is neuroprotective. Topical application of Netarsudil 3 times per day after rat optic nerve crush was neuroprotective, and these investigators showed reduction in p-cofilin, a biomarker of ROCK activation not only in retina, but in the optic nerve. These study methods are repeated to investigate neuroprotection by our combination therapy (API/Latanoprost) in an optic nerve crush model. In the first experiment, analogous to dosing of Netarsudil, test compound is applied topically 3 times daily. Four animals of each sex are tested per group, and statistics are with pooled animals for each treatment. Additional experiments powered to detect sex differences are carried out. During the course of experiments, animals are monitored daily for clinical signs, including hyperemia.

FIG. 8 shows enhanced RGC axon regeneration in an adult rat after treatment with racemic BA-1076. The optic nerve was crushed without affecting the ophthalmic artery and racemic BA-1076 was applied to the eye by intravitreal injection. Control animals were treated with phosphate-buffered saline (PBS) as vehicle control. Two weeks later the eye was injected with 0.5% of cholera toxin beta subunit, an anterograde neuronal tracer that labels neurons and their processes. Twenty-four hours later the rats were perfused through the heart with paraformaldehyde and the optic nerve removed. The optic nerve was mounted in medium, frozen in isopentane and cryostat sections prepared. The anterograde tracer was observed by immunofluorescent microscopy, which revealed that the BA-1076 treated eye showed enhanced regeneration.

EXAMPLE 11

Effect of ROCK Inhibitors on Vascularization and Angiogenesis

Inhibitors of ROCK are also known to affect the process of vascularization. Angiogenesis involves a complex concerted process which entails disruption of tissue matrix (allowing invasion), endothelial cell proliferation, migration and tube formation, orchestrated by local and inflammatory cells and followed by recruitment of mural cells. Numerous factors participate in angiogenesis, and some of these play major roles regardless of the tissue type. Retinal angiogenesis is one type which is one manifestation of diabetes.

To determine if BA-1076 (racemic) has an effect on retinal angiogenesis, an animal (rat) model was used. Rats are born with a completely avascular retina and the physiological retinal vascular development takes place in the first couple of weeks of their lives in a centripetal manner. At P6, 70% of their retina are physiologically vascularized. Sprague Dawley rat pups were injected intravitreally at P3 with 5 µl of 4 µg of racemic BA-1076 in 5 rats and the level of vascularization compared between the racemic BA-1076 treated (left) eye and the PBS injected right eye. The animals were sacrificed at P5. The eyes were fixed in 4% paraformaldehyde for 15 minutes at room temperature. Retinas were dissected and post-fixed in methanol for 10 minutes at −20° C. The retinas were incubated overnight with TRITC conjugated lectin griffonia *simplicifolia* (Sigma-Aldrich) diluted at 1/100 in 1% PBS Triton X-100. After washing, the retinas were mounted, viewed and photographed with a fluorescence microscope. The total surface and the surface of the vascularized area were measured using a computerized image-analysis system (image pro plus). Statistical analysis was performed using the paired t-test.

Figures 9B, 9C:
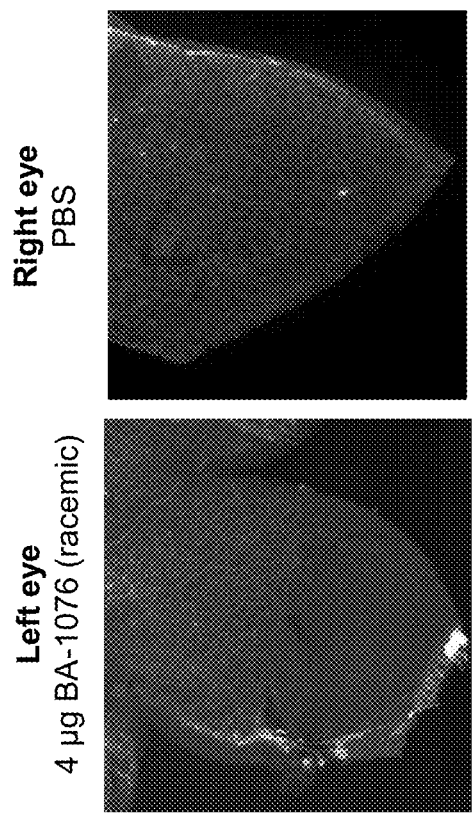
FIG. 9B is a fluorescence micrograph of a BA-1049-treated eye.
FIG. 9C is a fluorescence micrograph of a control PBS-treated eye.
Figure 9A:
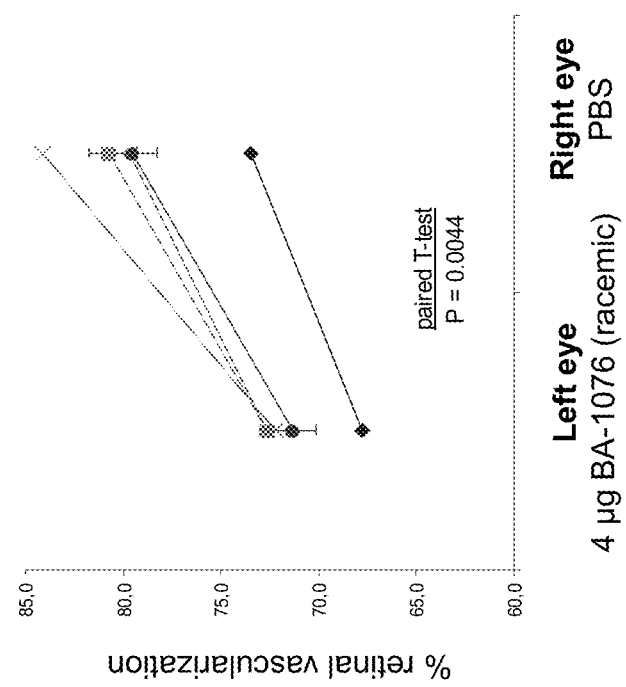
FIG. 9A is a graph showing the percent reduction in vascularization of rat eyes treated with BA-1076 (racemic) (left eye) compared with control eyes treated with PBS (right eye)

As shown in FIG. 9A and FIG. 9B, eyes treated with racemic BA-1076 showed statistically significant reduction in neovascularization.

Figure 10:
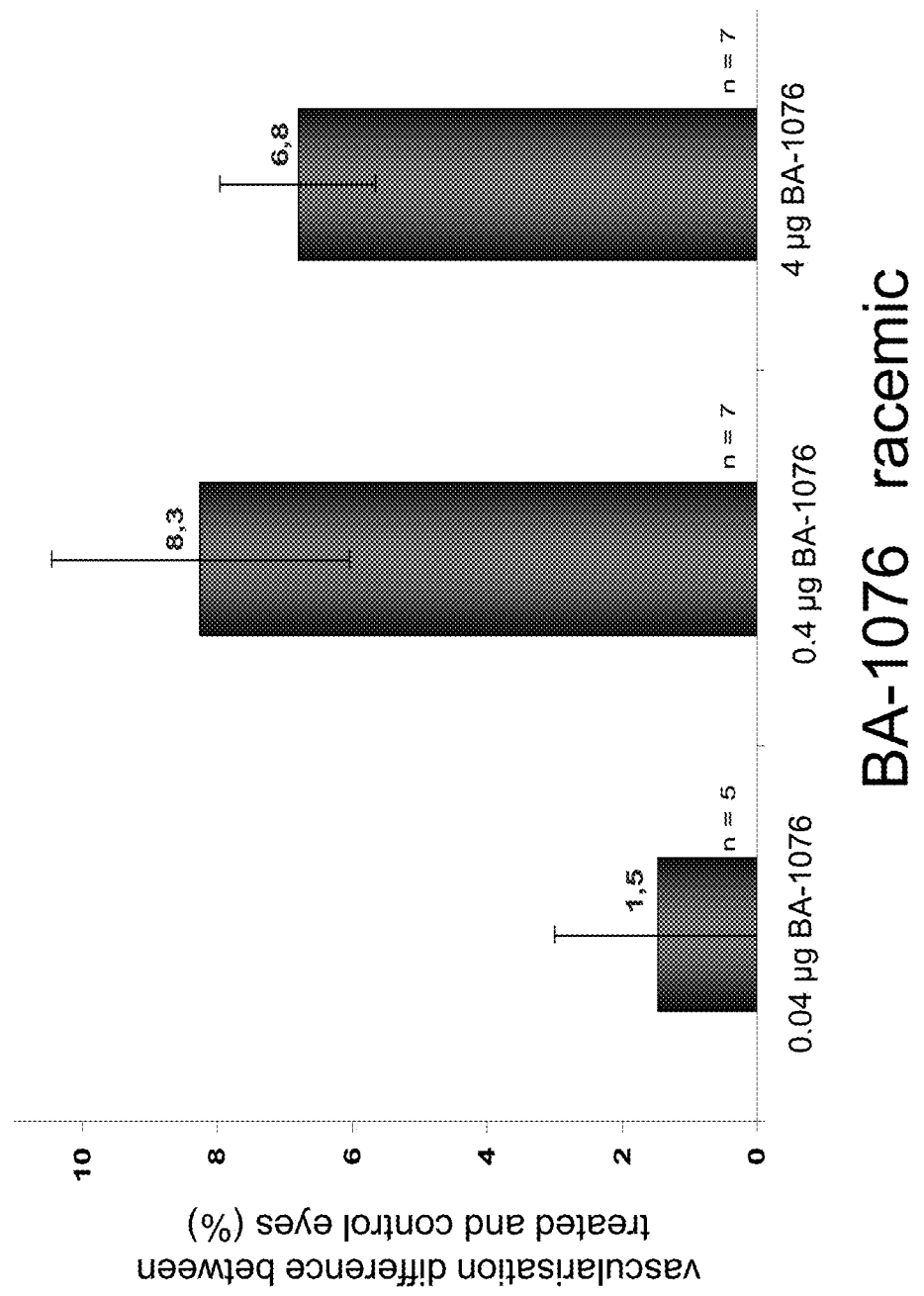
FIG. 10 is a graph showing the percent vascularization of rat eyes treated with 0.04 µg, 0.4 µg, or 4.0 µg BA-1076 (racemic)

In another experiment, the same model was used to examine the dose-response and doses of 0.04 µg, 0.4 µg, 4 µg, and 10 µg of BA-1076 (racemic) or PBS as vehicle control were tested in the same animal model. As shown in FIG. 10, all doses of racemic BA-1076 reduced neovascularization in the treated retina. Thus, racemic BA-1076 is a useful therapeutic for treating ocular neovascularization such as that which occurs in diabetes.

EXAMPLE 12

Retinitis Pigmentosa and Macular Degeneration

Mice homozygous for the RD1 mutation have an early onset retinal degeneration due to a mutation of the Pde6b gene encoding the beta subunit of cGMP-phosphodiesterase in rod photoreceptor. This mutation leads to toxic accumulation of the second messenger cGMP in the cell body, which causes photoreceptor cell death by apoptosis. In humans, a mutation in the same gene has been found to be responsible for a form of autosomal recessive retinitis pigmentosa (RP). RP is the most prevalent cause of registered visual handicap in those of working age in developed countries. In RD1 mice, degeneration starts around postnatal day 7-day 9 with complete disappearance of outer nuclear layer after in less than 4 weeks. The inner nuclear layer and the retinal ganglion cells appear normal but may show slight quantitative reduction. Although the eyes of the RD1 mice are devoid of normal rods, they retain some visual capacity but may suffer from night blindness. About 3% of cones among the visual cells degenerate at a much slower rate than do rods, so that a few cones are still present at 18 months. The RD1 mouse is useful as an animal model for retinal degeneration.

The ability of BA-1076 (racemic) to slow disease progression was tested in RD1 mice. For this study, 1 µL of 4 µg BA-1076 (racemic) was injected in the right eye of each mouse at postnatal day 12 and 1 µL of PBS injected into the left eye. The mice were euthanized at P15 and the eyes removed. After fixation in Bouin fixative, the eye specimens from the animals were dehydrated in graded alcohol series and embedded in paraffin for sectioning. Retinal sections were cut vertically through the optic disk at 5 µm thickness from nasal to temporal, and then the sections were stained with Hematoxylin and Eosin for 5 minutes in each stain. Hematoxylin stains tissue in a deep blue color while Eosin stains tissue in a deep red color allowing good visualization of the retinal layers. Retinal sections taken near the optic nerve were photographed and thickness of ONL or photoreceptor counts were measured at set distances from the optic nerve. Six to eight different pictures/animal were measured for each treatment.

Figure 11:
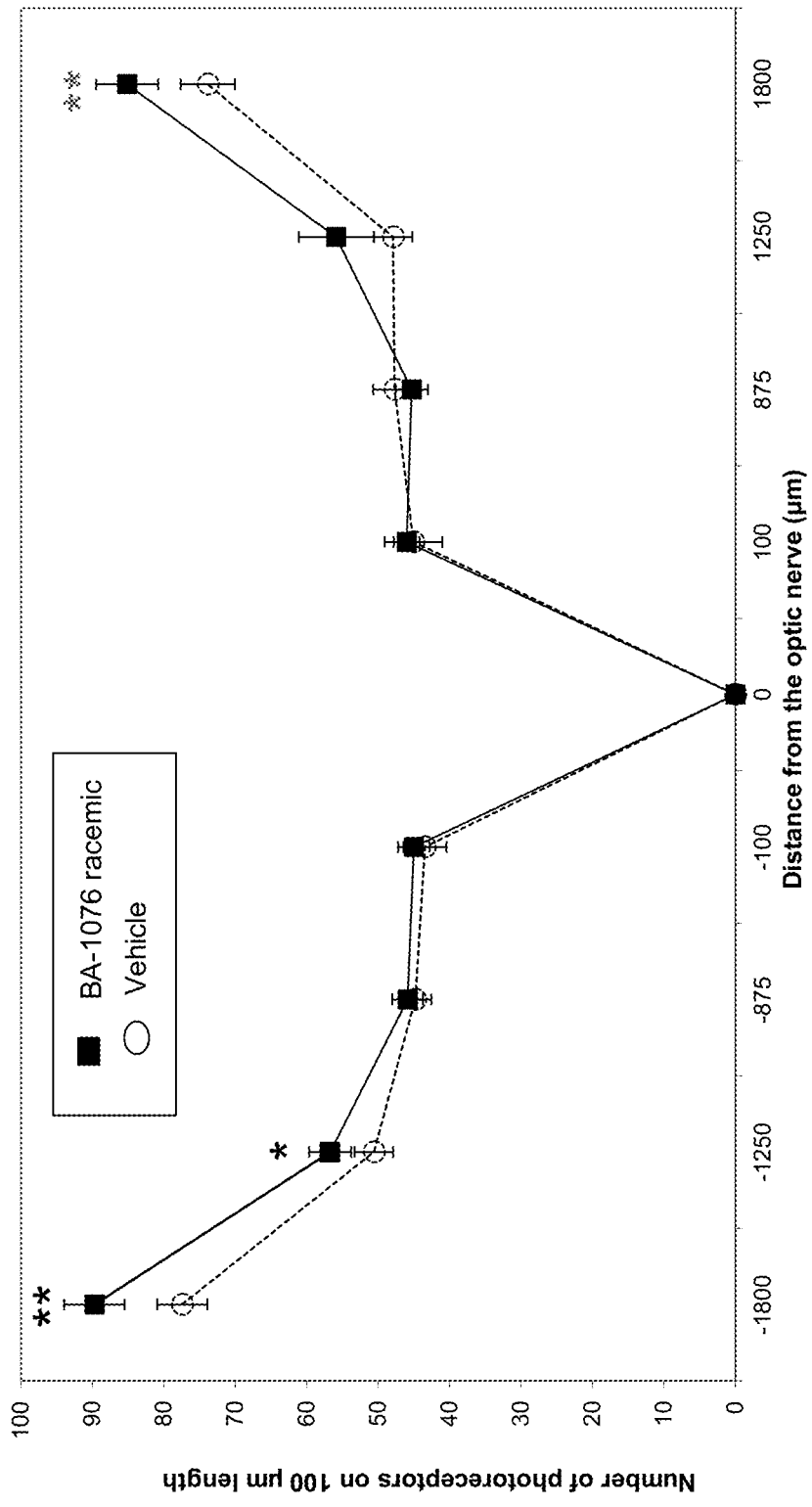
FIG. 11 is a graph showing the capability of racemic BA-1076 to slow the progression of retinal degeneration on RD1 mice, as evidenced by the number of photoreceptors at set distances from the optic nerve; n=5-7 mice per group. *P≤0.05, **P≤0.005

As shown in FIG. 11, BA-1076 (racemic) is neuroprotective for photoreceptors. Thus, a single intravitreal injection of racemic BA-1076 increases photoreceptor survival in a severe mouse model of retinal degeneration.

The "retinal degeneration" slow (or RDS) mouse is another useful animal model for human retinal degeneration. RDS is a mouse strain with a long-studied form of RP that is related to human mutations within the RDS-peripherin gene accounting for up to 10% of dominant cases of the disease. This gene normally produces a complex protein, critical to the function of light transduction by photoreceptors. The outer segments of the rod and cone photoreceptor cells of homozygotes fail to develop normally in RDS mice; eventually these cells degenerate and die. Degeneration in RDS mice has an early onset and slow progression. Half of the photoreceptors are lost between day 10 and day 42 and by 3 months of age, only 2-3 rows of nucleus are left in the ONL. The photoreceptor cell bodies and synaptic termini are eventually lost by apoptosis over a period of 12 months.

The ability of BA-1076 (racemic) to slow disease progression was tested in RDS mice. For this study, 1 µL of 5 µg BA-1076 (racemic) was weekly injected intravitreally in the right eye of each mouse and at the same time 1 µL of PBS was injected intravitreally into the left eye as control. Dosing began when mice were 1 month old and the eyes were injected weekly for 3 months, after which the mice were euthanized. The eyes were removed and fixed in Bouin fixative. The eyes were then dehydrated in graded alcohol series and embedded in paraffin for sectioning. Retinal sections were cut vertically through the optic disk at 5 µm thickness from nasal to temporal, and then the sections were stained with Hematoxylin and Eosin for 5 minutes in each stain. Hematoxylin stains tissue a deep blue while Eosin stains a deep red allowing good visualization of the retinal layers. Retinal sections taken near the optic nerve were photographed and thickness of ONL or photoreceptor counts were measured at set distances from the optic nerve. Six to eight different pictures/animals were measured for each treatment.

Figure 12:
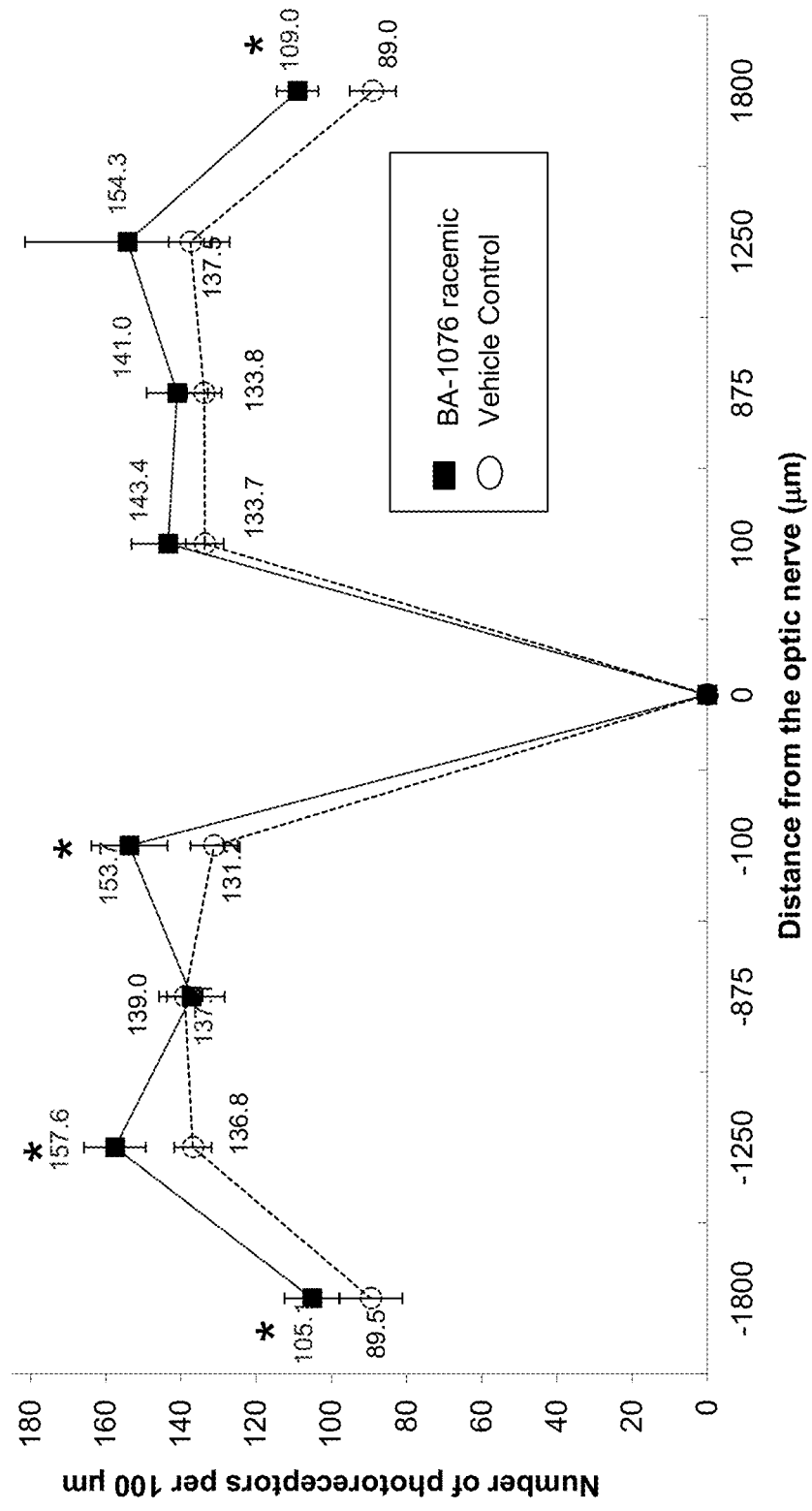
FIG. 12 is a graph showing the capability of racemic BA-1076 to slow the progression of retinal degeneration on RDS mice, as evidenced by the number of photoreceptors at set distances from the optic nerve.

As shown in FIG. 12, BA-1076 (racemic) is neuroprotective for photoreceptors in RDS mice. Thus, repeated weekly BA-1076 intravitreal injections increase photoreceptor survival in a mouse model of slow retinal degeneration.

EXAMPLE 13

Penetration of Compound in the Retina, Ocular Tissues, the Brain and Vascular Tissue The following experiment demonstrates the penetration and distribution of BA-1076 and its metabolite BA-2057 in rat ocular tissues after topical installation in the eye, and after delivery by oral or IV administration. Adult Sprague Dawley rats (Charles River Laboratories) were used for this experiment. Rat tissue was dissected out at 20 min to 48 hours after drug administration, and the concentration of BA-1076 and BA-2057 in homogenized brain tissue was measured using LC-MS/MS analysis. One g of tissue was homogenized in 1 mL of 1×PBS. Homogenates were precipitated by pipetting 200 µL of homogenate into a tube using aseptically cut off 1000 µL pipette tips to prevent clogging. Samples are further diluted with 100 µL PBS to aid in precipitation. 900 µL of cold methanol was added to each sample and samples were vortexed for 5 to 10 seconds. Samples were placed at 4° C. for 30 to 40 min and then centrifuged at 10,000 g for 15 min at 4° C. The supernatant is collected and stored at −80° C. until analyzed.

Figure 14:
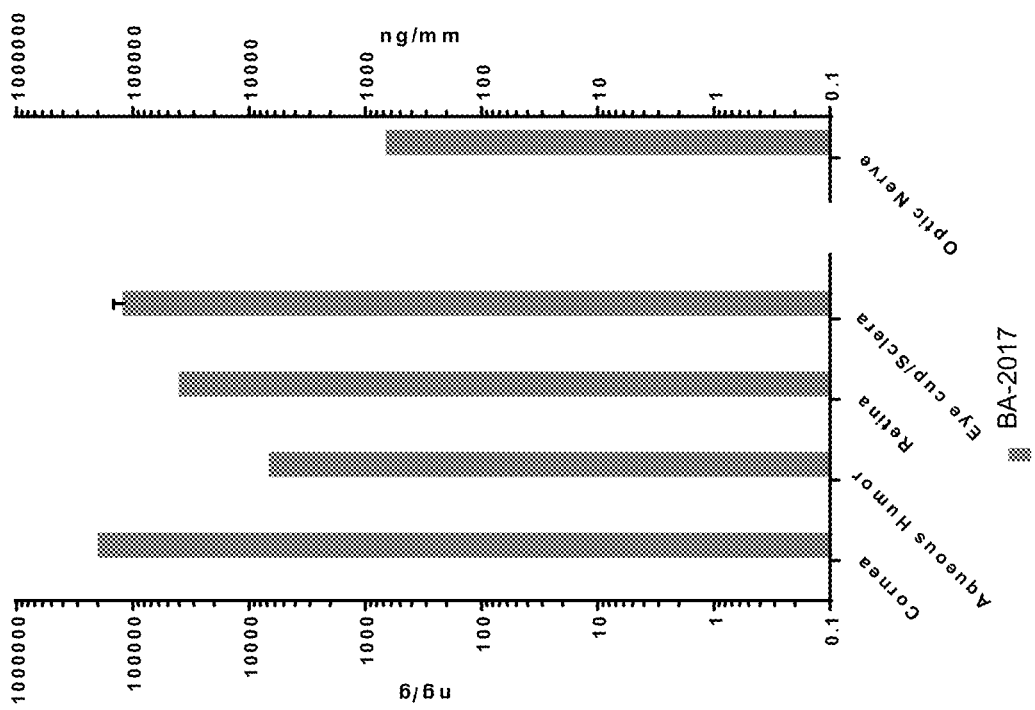
FIG. 14 is a graphic showing the exposure levels of BA-2017 after topical application of a 3% solution to the eye showing that the hydroxy metabolite can penetrate ocular tissue after tropical administration.

As shown in FIGS. 13 and 14, BA-1076 and its hydroxy-metabolite BA-2057 penetrate the tissue of the eye, including the CNS tissue of the retina. The tissue concentration of BA-1076 and active metabolite were determined after topical instillation of 5% solution of BA-1076 in the eye. Twenty minutes later the various ocular tissues were dissected, as shown in FIG. 13, and the concentration of BA-1076 and BA-2057 measured by LC-MS. For the optic nerve sample, the concentration is shown per length of optic nerve (right y-axis). These studies show that the metabolite is better able to penetrate the optic nerve, and may be actively transported into the optic nerve by the RGCs in the retina that are able to metabolize BA-1076 and that project their axons into the optic nerve. Therefore, drug is available in the retina and optic nerve for treating these tissues affected in glaucoma and other retinal diseases.

In FIG. 14 we examined the ability of metabolite to penetrate the ocular tissues of the eye after topical instillation of a 3% solution of metabolite. In comparison with FIG. 13, that also the metabolite has adequate penetration into ocular and CNS tissue. Of particular note is the penetration in the retina and presence in the optic nerve. All compounds were given topically as eye drops to the eye of adult Sprague Dawley rats. Twenty minutes later the indicated tissues were removed and the parent compound and active metabolite were analyzed by LC/MS. These results demonstrate that BA-1076 and BA-2057 distribute well in ocular tissues, which suggests these compounds suitable to treat or manage ocular diseases, disorders, or injuries.

Figure 15:
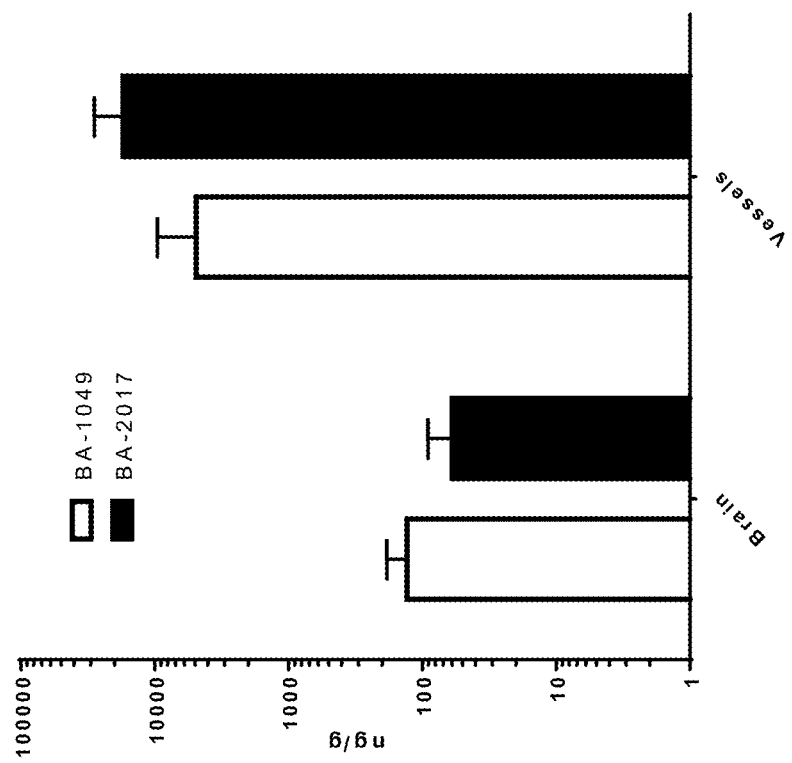
FIG. 15 is a graph showing brain penetrance of BA-1049 and BA-2017, and high exposure levels in blood vessels.
Figure 16A:
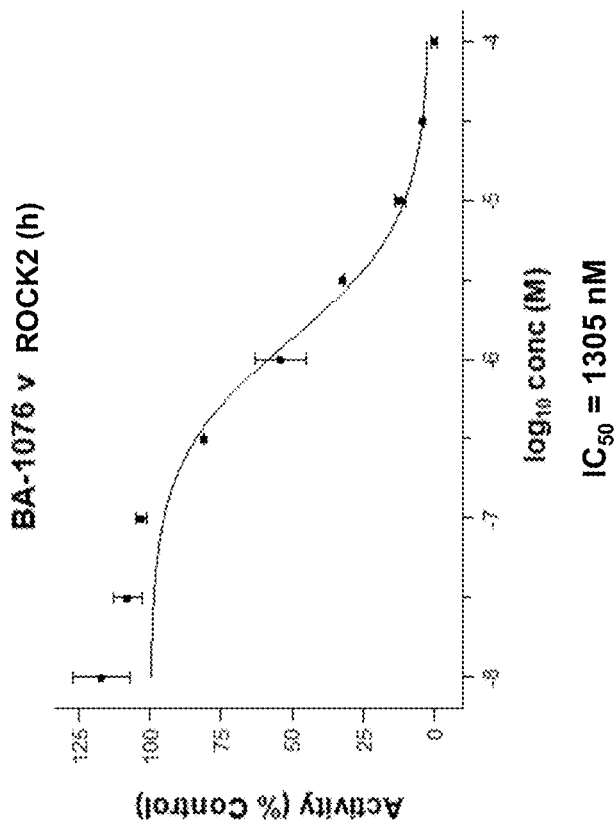
FIGS. 16A, 16B, 16C, and 16D are graphs showing BA-1076 $IC_{50}$ curves for ROCK1 and ROCK2. The data in FIGS. 16C and 16D were obtained using higher purity BA-1076 than in FIGS. 16A and 16B.
Figure 16B:
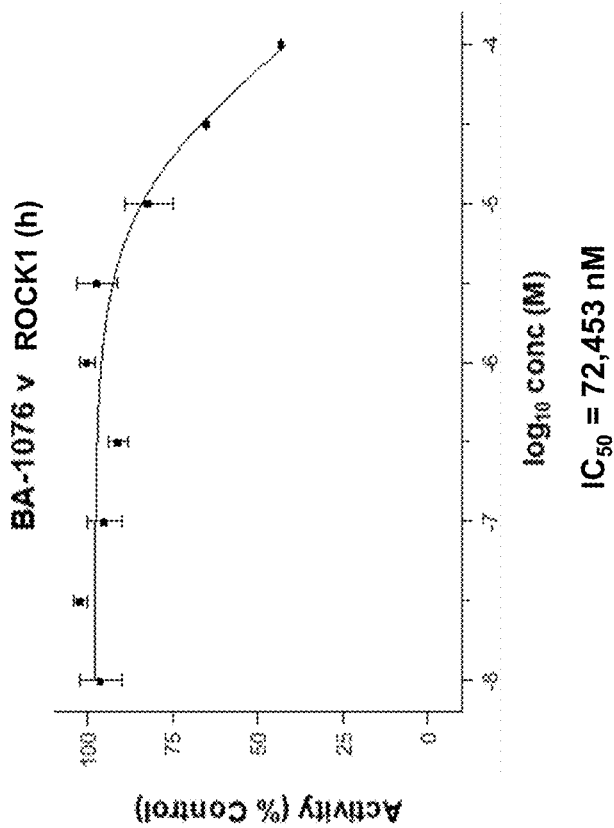
Figure 16D:
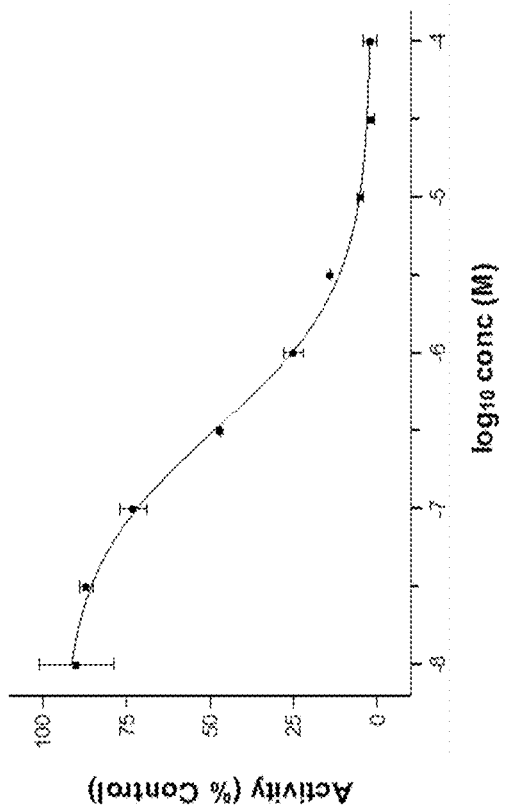
Figure 16C:
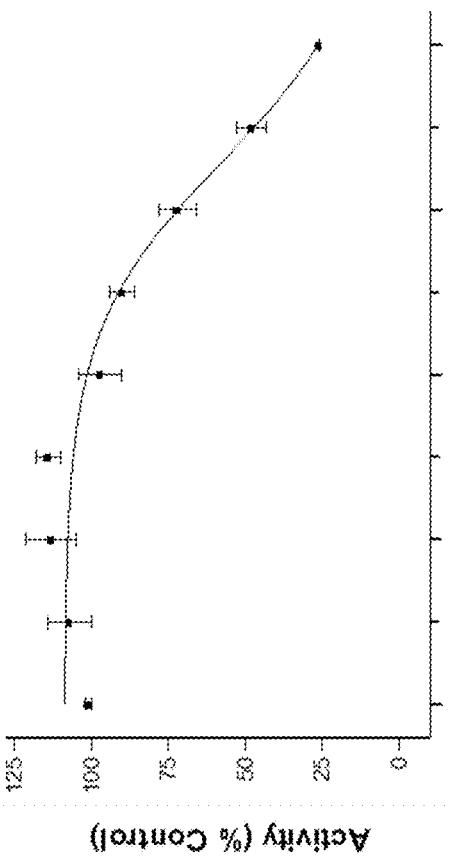
Figure 16F:
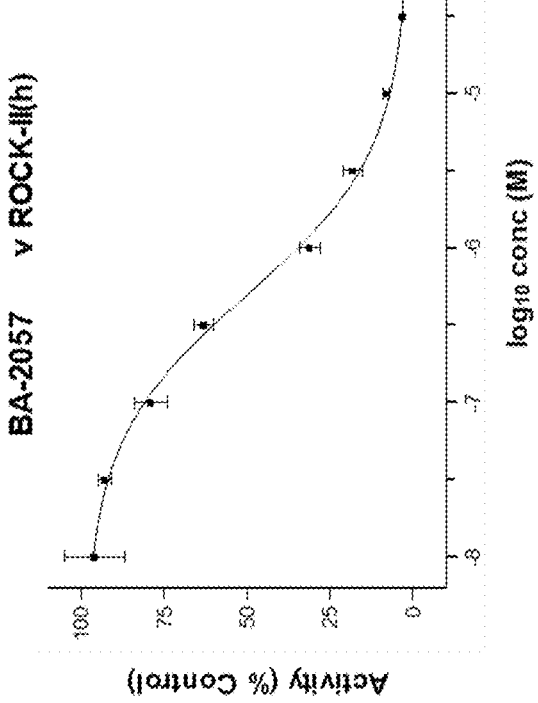
FIGS. 16E and 16F are graphs showing BA-2057 $IC_{50}$ curves for ROCK1 and ROCK2.
Figure 16E:
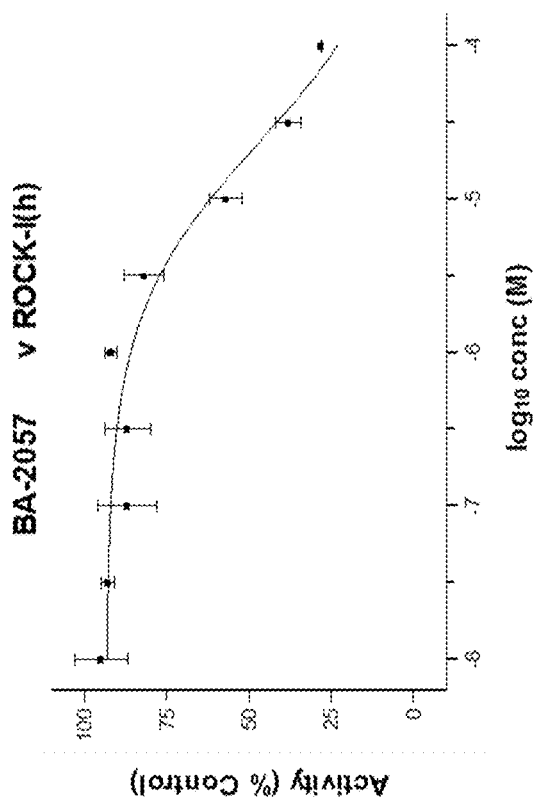

As shown in FIG. 15, BA-1049, the R enantiomer of BA-1076, and its active metabolite (BA-2017) were present in the brain after oral administration, which demonstrates that BA-1049 is able to cross the blood brain barrier.

As shown in FIG. 15, BA-1049 and its active metabolite BA-2017 accumulate at high concentrations in blood vessels after oral administration. Pathological angiogenesis that occurs in the retina is a major feature of leading blinding diseases, and particularly associated with diabetic retinopathy and age-related macular degeneration.

As BA-1049 and BA-2017 are enantiomers of BA-1076 and BA-2057, respectively, these results strongly suggest that BA-1076 and BA-2057 are suitable compounds to treat or manage CNS diseases, disorders, or injuries as well as vascular diseases or disorders.

Neurological Diseases

EXAMPLE 14

In Vitro Effect of Rho Kinase Inhibitors and Abl Kinase Inhibitors on Dopaminergic Neurons The following experiment demonstrates the ability of rho kinase inhibitors and Abl kinase inhibitors to protect midbrain dopaminergic neurons in culture from the well-known toxic effects of the chemical MPP+ (1-methyl-4-phenylpyridinium). MPP+ is a known dopaminergic neurotoxin. Previous studies have shown that this compound causes the overactivation of the c-Abl non-receptor tyrosine kinase which then phosphorylates the Parkin E3 ubiquitin ligase leading to its inactivation (Ko et al., Proc. Nat. Acad. Sci. USA; 2010; 107:16691). Additionally, this neurotoxin is also known to cause the activation of Rho kinase (ROCK) in the brain when administered to animals (Rodriguez-Perez et al., Neurobiol. Dis., 2013; 58:209).

These in vitro experiments are conducted using primary cultures of embryonic rat midbrain dopaminergic neurons. MPP+ is known to cause the death of cultured midbrain dopaminergic neurons. Rho kinase and Abl kinase inhibitors are tested individually at varying concentrations for their ability to prevent MPP+-induced cell death.

Primary cultures of rat midbrain dopaminergic neurons are established from cells acutely isolated from the ventral midbrain of embryonic day 14 rats (Charles River; Wilmington, Mass.). The cells are plated in serum-free conditions (Neurobasal plus B-27 Supplements; Thermo-Fisher; Waltham, Mass.) onto glass coverslips coated with poly-ornithine and laminin as attachment factors. Cells are cultured overnight on the coated coverslips in a 37° C./5% CO2 tissue culture incubator prior to the initiation of the varying treatments.

Beginning on day 2 after plating, either vehicle solution or varying concentrations of BA-1076 or BA-2057 (0.25, 0.5, 1, 5, 10, 20, or 50 µM) are added to the medium of the neuronal cultures. On day 3 after plating, MPP+(Sigma Chemical; St. Louis, Mo.) is added to the medium at 20 µM final concentration. The cultures are allowed to continue for an additional 48 hours. At the end of the culture period, the cells are washed, and then fixed with 4% paraformaldehyde solution prior to permeabilization and blocking with 10% normal goat serum in PBS. The cells are incubated overnight with antibodies against tyrosine hydroxylase (TH) (rabbit anti-TH; EMD-Millipore; Billerica, Mass.), a cell-specific marker of midbrain dopaminergic neurons. The following day, the cultures are reacted with a fluorescent Cy3-conjugated goat-anti-rabbit secondary antibody (Jackson ImmunoResearch; West Grove, Pa.). The coverslips are mounted onto microscope slides along with VectaShield anti-fade mounting medium with DAPI (Vector Labs) to visualize the nuclei. Specimens are examined using fluorescence microscopy and the numbers of TH-positive neurons with non-pyknotic nuclei are counted in 6 to 8 high power fields per specimen.

Analysis of the numbers of TH-positive neurons with normal nuclei demonstrates that treatment with BA-1076 or BA-2057 leads to a dose-dependent increase in the number of surviving neurons in culture following exposure of the neurons to MPP+ as compared to vehicle identifying the ability of BA-1076 and BA-2057 to combat the toxicity of MPP+.

EXAMPLE 15

In Vivo Effect of Rho Kinase and Abl Kinase Inhibitors on Dopaminergic Neurons

The following experiment demonstrates the ability of certain rho kinase and Abl kinase inhibitors to protect midbrain dopaminergic neurons in vivo in the intact mouse from the well-known toxic effects of the chemical MPTP (1-methyl-4-phenyl-1,2,3,6-tetrahydropyridine). These in vivo experiments are conducted using adult C57BL/6 mice (a strain specifically selected because of their sensitivity to MPTP) to determine the ability of BA-1076 and BA-2057 to protect midbrain dopaminergic neurons from the cell death typically induced by administration of MPTP. Previous studies have shown that this compound causes the overactivation of the c-Abl non-receptor tyrosine kinase in these neurons, which then phosphorylates the Parkin E3 ubiquitin ligase leading to its inactivation (Ko et al., Proc. Nat. Acad. Sci. USA; 2010; 107:16691). Additionally, this neurotoxin is also known to cause the activation of Rho kinase (ROCK) in the brain when administered to animals (Rodriguez-Perez et al., Neurobiol. Dis., 2013; 58:209).

Different cohorts of adult C57BL/6 mice (Charles River; Wilmington, Mass.) (8 to 10 per group) receive intraperitoneal injections of either vehicle or 30 mg/kg of MPTP (Sigma; St. Louis, Mo.) dissolved in 0.9% saline for 5 consecutive days. This sub-acute/chronic treatment regimen typically leads to the death of 40 to 50% of midbrain dopaminergic neurons of the substantia nigra within 1 to 2 weeks (Meredith and Rademacher; J Parkinsons Dis.; 2011; 1(1):19).

Beginning one day prior to the first MPTP or vehicle injection, different cohorts of mice begin treatment with either 10 or 100 mg/kg per day in their drinking water of BA-1076 or BA-2057 or simply water for the extent of the experiment. The cohorts are carried forward for 14 days. On the final 2 days of the treatment paradigm, mouse cohorts are subjected to behavioral testing using the accelerated rotarod on one day or grid-walking test on the other day. At completion of the final behavioral test, animals are deeply anesthetized and then perfused transcardially with 4% paraformaldehyde in phosphate buffer. Brains are removed from the craniums and post-fixed for 1-2 hours. The brains are then immersed in 30% sucrose for cryo-protection. Whole coronal sections (20-25 µm thick) through the midbrain region containing the substantia nigra are obtained for each animal and thaw mounted onto SuperFost Plus slides (Thermo-Fisher). Individual sections are reacted with rabbit anti-tyrosine hydroxylase (TH) antibody (EMD-Millipore) overnight in PBS containing 0.05% Triton X-100 and 10% normal goat serum. After washing in PBS/Triton-X-100 multiple times, sections are reacted with HRP-conjugated goat anti-rabbit secondary antibody. Following another round of washing, the slides are reacted with Vecta Stain Elite ABC kit for DAB-enhanced peroxidase detection (Vector Labs; Burlingame, Calif.). Following peroxidase reaction, the sections are subjected to Nissl staining to label all cell types as a counterstain. The sections are then coverslipped in permanent mounting media.

Sections are examined by visible microscopy and photographic images captured. The number of TH positive neurons are estimated in the series of images by unbiased stereological analysis using Stereo Investigator. Numbers of TH-positive neurons per area of the substantia nigra are determined and statistical analyses performed to compare between, control untreated, MPTP/no treatment, MPTP/inhibitor treatments.

The analyses demonstrate that MPTP-treated mice receiving treatment with either BA-1076 or BA-2057 have improved motor function in behavioral testing as compared to those with no treatment. Additionally, histological examination of the region of the substantia nigra indicates that BA-1076 and BA-2057 prevent a significant percentage of the cell loss due to the neurotoxic effects of MPTP treatment as a model of Parkinson disease.

EXAMPLE 16

$IC_{50}$ Analysis of BA-1076 versus ROCK1 and ROCK2 to Assess Selectivity

The selectivity of BA-1076 for inhibition of ROCK1 and ROCK2 was tested by an enzyme inhibition assay to identify the concentration at which the compound reduces the enzymatic activity of the enzymes by 50%, the half-maximal inhibitory concentration or $IC_{50}$. $IC_{50}$ determinations for BA-1076 were performed using a proprietary direct filter-binding radiometric kinase assay over a 9-point half-log dilution scale at Eurofins Testing (Dundee, Scotland, UK). ROCK1 and ROCK2 $IC_{50}$ determinations were made using ATP concentrations at the Km ATP of 70 µM and 15 µM for ROCK1 and ROCK2, respectively. BA-1076 was tested for its inhibitory effects against ROCK1 and ROCK2 at concentrations ranging from 100 µM down to 10 nM.

As shown in FIGS. 16A, 16B, 16C, and 16D, the IC50 plots against ROCK1 and ROCK2 identify a significant selectivity of BA-1076 for the ROCK2 isoform, as evidenced by the leftward shift in the inhibition curve when ROCK2 is compared to ROCK1. Calculation of the apparent IC50 in this experiment showed that BA-1076 inhibited ROCK1 with an IC50 of 72,453 nM and inhibited ROCK2 with an apparent IC50 of 1305 nM.

BA-1049, BA-2017, and BA-2057 have also been tested in this assay, and BA-1076 assay was repeated. The data are shown in Table 4.

TABLE 4

| Compound | ROCK1 $IC_{50}$ (nM) | ROCK2 $IC_{50}$ (nM) | ROCK1/ROCK2 (fold difference) |
|---|---|---|---|
| BA-1076 | 72453 | 1305 | 55.5 |
| BA-1076* | 19590 | 322 | 60.8 |
| BA-1049 | 26009 | 599 | 43.4 |
| BA-2017 | 3026 | 183 | 16.5 |
| BA-2057 | 23582 | 491 | 48.0 |

*data were obtained for higher purity BA-1076.

For the data shown in Table 4, IC50 inhibition curves were performed at the respective Km for ATP for both ROCK1 and ROCK2. Performing these assays at the Km of ATP gives a better representation of the inhibitory activity. Other comparisons where differing kinases are tested at a single ATP concentration can potentially misrepresent the comparative efficacy since enzyme inhibitory activity tested below the Km for ATP of the enzyme, produces a circumstance where the enzyme is actually not constantly bound with ATP and the reaction velocity becomes sub-optimal.

EXAMPLE 17

Ability of BA-1076 and BA-2057 to Reduce Amyloid Beta and Phosphorylated Tau Levels In Vitro Alzheimer's disease is the most common cause of dementia in the population. Pathologic hallmarks of the disease include the presence in the brain of beta-amyloid bearing plaques and neurofibrillary tangles containing hyperphosphorylated microtubule-associated protein Tau. The 3×-Tg AD mouse model was developed to serve as a rodent model for the development of the biochemical hallmarks of human Alzheimer's disease. This mouse strain harbors 3 transgenes encoding mutant Presenilin-1 (PS1), human Swedish mutant Amyloid Precursor Protein (APP-Swe), and mutant P301L-Tau and is obtained from Jackson Laboratories (Bar Harbor, Me.). Primary cultures of cortical neurons from postnatal day 1 mice are used to assess the ability of BA-1076 and BA-2057 to limit the production of both beta-amyloid and phosphorylated forms of Tau. Previous studies have indicated that changes in ROCK2 can modulate beta-amyloid production in neurons from the 3×-Tg AD mice and that increased ROCK levels are seen in AD brain (Herskowitz et al.; J. Neurosci.; 2013; 33(49):19086). Similarly, Cancino et al (Cancino et al.; Neurobiol. Aging; 2011; 32:1249) identified the role of increased c-Abl kinase activity in transgenic AD model mice to direct increased phosphorylation of Tau. Therefore, this experiment will test whether BA-1076 and BA-2057 would have utility in preventing both the accumulation of beta-amyloid and hyperphosphorylated Tau in cultured primary cortical neurons in vitro.

Whole brain cortices from one day old (P1) 3×-Tg AD mice (Jackson Labs) are dissected and then dissociated using trypsinization and trituration before being cultured under serum free conditions (NeuroBasal Medium plus B27 supplements; Thermo-Fisher) on dishes pre-coated with poly-ornithine and laminin as growth substrate. The cultures are plated in 24 well tissue culture plates, with 100 to 200,000 cells per well at plating. Cultures are maintained for 5 to 7 days, with half-volume medium changes every other day, before testing of inhibitor treatments. Cultures are then treated for 24 or 48 hours with 1, 10 or 50 µM BA-1076 or BA-2057 or vehicle. Protein extracts are prepared in RIPA buffer and protein concentrations in each extract are determined using the Pierce BCA assay (Pierce Biotechnology). Equivalent amounts of protein from each extract are separated on 4-12% polyacrylamide Bis-Tris gels run in MES buffer (Thermo-Fisher). After transferring to PVDF membranes, the Western blots are processed to examine the levels of beta-amyloid precursor protein (βPAPP), the peptide β-amyloid (Aβ), and levels of both phosphorylated and total tau protein.

For these Western blotting experiments, hyperphosphorylated Tau is detected using antibody AT8-phospho-Ser-202/Thr-205 (Pierce Biotechnology, Rockford, Ill.); total phosphorylated and nonphosphorylated tau is detected with Tau5 antibody (Calbiochem, San Diego, Calif.); total PAPP is detected using monoclonal antibody 22C11 (EMD-Millipore) and Aβ peptide levels are detected using monoclonal antibody 6E10 (BioLegend; San Diego, Calif.). The form of Aβ present can be estimated by comparison to purified Aβ 1-40, 1-42 peptides (AnaSpec; Fremont, Calif.) run as standards on companion gels.

Inhibition of ROCK2 and optionally c-Abl by either BA-1076 or BA-2057 show a dose-dependent reduction in the accumulation of phosphorylated forms of Tau protein and a reduced production of Aβ peptide in cultured cortical neurons from 3×-Tg AD mice.

EXAMPLE 18

Treatment of Acute Irradiation Syndrome (ARS)

A mouse model of total body irradiation (TBI) is used to assess efficacy of BA-1076 and BA-2057 for treating radiation injury. At day 0, TBI is carried out at a lethal dose of 8.0 Gy (Harlan mice) or 9.0 Gy (Coats mice)-doses that are expected to cause death in about 90% of animals within 30 days. Mice receive oral BA-1076 or IV BA-2057 injections in doses ranging from 0.1 mg/kg to 30 mg/kg at 24 hours, 48 hours, and 72 hours after irradiation. Mice are monitored for survival up to day 30. During this period, mice were deprived of all supportive care, including antibiotics, to increase the stringency of the survival protocol. Survival is assessed with Kaplan-Meir curves. For GI histopathology studies, mice are subjected to TBI at 8.0 Gy (Harlan mice) and administered either placebo, BA-1076 or BA-2057 for three days. Mice are euthanized at 3 days and GI tissue is paraffin-embedded, sectioned and immunolabeled with rabbit anti-mouse leucine-rich-repeat-containing G-protein-coupled receptor 5 (LGR5), a GI stem cell marker that is expressed upon GI injury. Exposure to TBI (8.6 Gy), resulted in substantial jejunal damage 3 days after irradiation, as evidenced by the widespread expression of LGR5. Administration of BA-1076 or BA-2057 mitigated radiation-induced jejunal damage, with no LGR5 expression evident at the optimal, efficacious dose.

Other Embodiments

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A therapeutic composition comprising a therapeutically effective amount of a compound of formula:

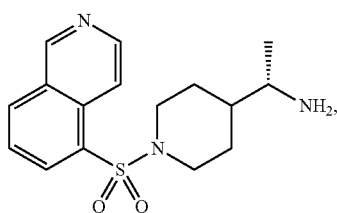

BA-1076 or a pharmaceutically acceptable salt thereof,
wherein BA-1076 or a pharmaceutically acceptable salt thereof is present in at least 10% enantiomeric excess.

2. The therapeutic composition of claim 1, further comprising a therapeutically effective amount of a compound of formula:

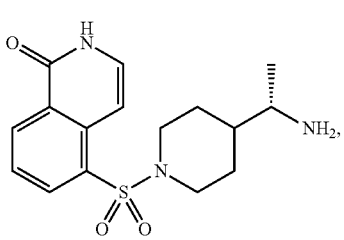

BA-2057 or a pharmaceutically acceptable salt thereof,
wherein BA-2057 or a pharmaceutically acceptable salt thereof is present in at least 10% enantiomeric excess.

3. A therapeutic composition comprising a therapeutically effective amount of a compound of formula:

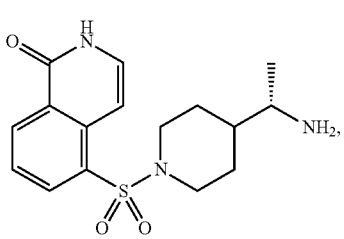

BA-2057 or a pharmaceutically acceptable salt thereof,
wherein BA-2057 or a pharmaceutically acceptable salt thereof is present in at least 10% enantiomeric excess.

4. The therapeutic composition of claim 3, wherein BA-2057 is present in at least 50% enantiomeric excess.

5. The therapeutic composition of claim 1, wherein BA-1076 is present in at least 50% enantiomeric excess.

6. The therapeutic composition of claim 1, further comprising latanoprost, travaprost, bimatoprost, or tafluprost.

7. The therapeutic composition of claim 1, wherein the therapeutic composition is formulated for ocular topical administration, intravitreal administration, intraocular administration, retinal administration, oral administration, or intravenous administration.

8. The therapeutic composition of claim 7, wherein the therapeutic composition is in a dosage form of eye drops, formulated for oral administration, or formulated for intravenous administration.

9. The therapeutic composition of claim 1, wherein the therapeutic composition comprises the compound at a concentration of 0.001% to 5% (w/v) or at a dose of 0.01 mg/kg to 10 mg/kg.

10. A method of treating glaucoma, retinitis pigmentosa, macular degeneration, or retinal angiogenesis in a subject in need thereof, comprising administering to the subject a therapeutically-effective amount of the therapeutic composition of claim 1.

11. The method of claim 10, wherein the method is for treating glaucoma in the subject.

12. The method of claim 10, wherein the therapeutic composition is administered topically, intravitreally, intraocularly, retinally to the eye, orally, or intravenously.

13. The method of claim 10, wherein the method further comprises administering travaprost, bimatoprost, latanoprost, or tafluprost.

14. The method of claim 10, wherein the method of treating corneal scarring comprises reducing post-operative corneal scarring in a subject in need thereof.

15. The therapeutic composition of claim 3, further comprising latanoprost, travaprost, bimatoprost, or tafluprost.

16. A method of treating glaucoma, retinitis pigmentosa, macular degeneration, or retinal angiogenesis in a subject in need thereof, comprising administering to the subject a therapeutically-effective amount of the therapeutic composition of claim 3.

17. The method of claim 16, wherein the method is for treating glaucoma in the subject.

18. The method of claim 16, wherein the therapeutic composition is administered topically, intravitreally, intraocularly, retinally to the eye, orally, or intravenously.

19. The method of claim 16, wherein the method further comprises administering travaprost, bimatoprost, latanoprost, or tafluprost.

* * * * *